US007049065B2

(12) United States Patent
Hayashizaki

(10) Patent No.: US 7,049,065 B2
(45) Date of Patent: May 23, 2006

(54) METHOD OF PREPARING NORMALIZED AND/OR SUBTRACTED CDNA

(75) Inventor: Yoshihide Hayashizaki, 22-1-201, Inarimae, Tukuba-shi, Ibaraki 305-0061 (JP)

(73) Assignees: Yoshihide Hayashizaki, Tsukuba (JP); Riken, Wako (JP)

(*) Notice: Subject to any disclaimer, the term of this patent is extended or adjusted under 35 U.S.C. 154(b) by 0 days.

(21) Appl. No.: 09/935,592

(22) Filed: Aug. 24, 2001

(65) Prior Publication Data

US 2002/0106666 A1 Aug. 8, 2002

(30) Foreign Application Priority Data

Aug. 25, 2000 (JP) .............................. 2000-255402

(51) Int. Cl.
*C12Q 1/68* (2006.01)
*C12P 19/34* (2006.01)
*C07H 21/02* (2006.01)

(52) U.S. Cl. .................... 435/6; 435/91.1; 435/91.2; 536/23.1; 536/24.3

(58) Field of Classification Search ................ 435/6, 435/91.1, 91.2; 536/23.1, 24.3
See application file for complete search history.

(56) References Cited

U.S. PATENT DOCUMENTS

| 5,585,242 A | * | 12/1996 | Bouma et al. ................. 435/6 |
| 5,846,721 A | | 12/1998 | Soares et al. |
| 5,891,637 A | * | 4/1999 | Ruppert ............................ 435/6 |
| 5,955,594 A | * | 9/1999 | Mishra ...................... 536/23.5 |
| 6,090,548 A | * | 7/2000 | Lavery et al. ................. 435/6 |
| 6,143,874 A | * | 11/2000 | Chang ...................... 530/387.9 |

FOREIGN PATENT DOCUMENTS

WO 96/21743 7/1996

OTHER PUBLICATIONS

Carninci et al, "Normalization and subtraction of Cap-trapper selected cDNAs to prepare full length cDNA libraries for rapid discovery of new genes", Genome Research (2000) 10:1617-1630.*

Carninci et al, "High efficiency full length cDNA cloning by Biotinylated CAP trapper", Genomics (1996) 37:327-336.*

(Continued)

*Primary Examiner*—Jeffrey Fredman
(74) *Attorney, Agent, or Firm*—Birch, Stewart, Kolasch & Birch, LLP

(57) ABSTRACT

A method of preparing normalized and/or subtracted cDNA; a method in which the cDNA that is normalized and/or subtracted is in the form of uncloned cDNA (cDNA tester); a method of preparing normalized and/or subtracted cDNA comprising the steps of: (a) preparing cDNA tester; (b) preparing normalization and/or subtraction RNA driver; (c) conducting normalization and/or subtraction in two steps in any order, or conducting normalization/subtraction as a single step and mixing the normalization/subtraction RNA driver with said cDNA tester; (d) adding an enzyme capable of cleaving single strand sites on RNA drivers nonspecifically bound to cDNA tester; (e) removing said single strand RNA driver cleaved in step d) from the tester and removing tester/driver hybrids; and (f) recovering the normalized and/or subtracted cDNA; and a method of efficiently preparing normalized and/or subtracted long-chain, full-coding, and full-length cDNA libraries are provided.

76 Claims, 6 Drawing Sheets

OTHER PUBLICATIONS

C.G. Sagerstrom et al., "Subtractive Cloning: Past Present, and Future", Annual Review of Biochemistry, vol. 66, 1997, pp. 751-783.

Piero Carninci et al., "High Efficiency Selection of Full-length cDNA by Improved Biotinylated Cap Trapper", DNA Research, vol. 4, No. 1, 1997, pp. 61-66.

Hiroko Shibata et al., Representative normalized and subtracted cDNA libraries for the construction of the full-length cDNA encyclopedia, Nippon Bunshi Seibutsu Gakkai Nenkai Program Kouen Youshishuu, vol. 1, 1998, pp. 322.

Katherine J. Martin et al., "Identifying expressed genes", PNAS, vol. 97, No. 8 (Apr. 2000), pp. 3789-3791.

Maria de Fatima Bonaldo et al., "Normalization and Subtraction: Two Approaches to Facilitate Gene Discovery", Genome Research, XP002039972 (1996), pp. 791-806.

* cited by examiner

SEQUENCE LISTING

```
<160> NUMBER OF SEQ ID NOS: 7

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: first-
      strand primer comprising BamHI and SstI restriction sites
<221> NAME/KEY: misc_feature
<222> LOCATION: (42)
<223> OTHER INFORMATION: Nucleotide 42 is v wherein v = g or c or a
<221> NAME/KEY: misc_feature
<222> LOCATION: (43)
<223> OTHER INFORMATION: Nucleotide 43 is n wherein n = any nucleotide

<400> SEQUENCE: 1
gagagagaga aggatccaag agctcttttt ttttttttt tvn              43

<210> SEQ ID NO 2
<211> LENGTH: 49
<212> TYPE: DNA
<213> ORGANISM: Artificial Sequence
<220> FEATURE:
<223> OTHER INFORMATION: Description of Artificial Sequence: primer
      comprising the XhoI restriction site

<400> SEQUENCE: 2
gagagagaga gagattctcg agttaattaa attaatcccc ccccccccc        49

<210> SEQ ID NO 3
<211> LENGTH: 55
<212> TYPE: DNA
<213> ORGANISM: Artificial Sequence
<220> FEATURE:
<223> OTHER INFORMATION: Description of Artificial Sequence: primer
      comprising the SstI restriction site

<400> SEQUENCE: 3
```

```
gagagagaga gagagagaga gctcactagt ttaattaaat taatccccc ccccc          55

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: primer
      comprising the XhoI restriction site
<221> NAME/KEY: misc_feature
<222> LOCATION: (40)
<223> OTHER INFORMATION: Nucleotide 40 is v wherein v = g or c or a
<221> NAME/KEY: misc_feature
<222> LOCATION: (41)
<223> OTHER INFORMATION: Nucleotide 41 is n wherein n = any nucleotide

<400> SEQUENCE: 4
gagagagaga gagagaactc gagttttttt ttttttttv n                         41

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: M13 forward
      primer

<400> SEQUENCE: 5
tgtaaaacga cggccagt                                                  18

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: 1233REV
      reverse primer

<400> SEQUENCE: 6
agcggataac aatttcacac agga                                           24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: SK primer

<400> SEQUENCE: 7
cgctctagaa ctagtggatc                                                20
```

METHOD OF PREPARING NORMALIZED AND/OR SUBTRACTED CDNA

TECHNICAL FIELD

The present invention relates to an improved method of preparing normalized and/or subtracted cDNAs or cDNA libraries.

The present invention also relates to a method for improvement of the normalization and subtraction steps by eliminating non-specifically bound hybrids.

BACKGROUND OF THE ART

Methods of preparing cDNA libraries have been disclosed and are well known in prior art. For example, they are described by Ederly I., et al., 1995, Mol Cell Biol, 15:3363–3371; Kato S., et al., 1994, Gene, 150:243–250; and K. Maruyama et al., 1995, Gene, 138:171–174.

In prior art, Carninci et al., 1996, Genomics 37:327–336; Carninci et al., 1997, DNA Research, 4:61–66; and Carninci and Hayashizaki, 1999, Methods Enzymol, 303: 1–44, describe efficient methods for the preparation of cDNAs. These methods, comprising a modified "tagged cap trapper" to select long-strand, full-coding and/or full-length cDNA libraries after tagging of the cap structure, allow the preparation of long, full-coding and/or full-length cDNA libraries containing all of a particular coding sequence and its 3' and 5' untranslated regions (UTRs). Such libraries are particularly useful for large-scale sequencing projects in which the recovery of long, full-coding and/or full-length (full-coding/length) clones is required from among truncated clones (EST sequences).

However, the preparation of long, full-coding/length cDNA libraries entails certain problems. The preparation of long or full-coding/length cDNA is more efficient for short-strand mRNAs than for long-strand mRNAs (transcripts). In addition, cloning and amplification is more difficult for long-strand cDNAs than for short-strand cDNAs, further introducing size bias. Using truncated cDNAs to recover full-length cognates is impractical at the genomic-scale level; however, cDNAs in a standard library can be cloned in either their long, full-coding/length or truncated form, thus favoring discovery of at least one EST for any gene, regardless of length.

Another problem relates to the nature of cellular mRNA. mRNA can be classified into superprevalent (or abundant), intermediate and rare mRNA based on expression. In a typical cell, 5–10 species of superprevalent mRNA comprise at least 20 percent of the amount of mRNA, 500 to 2,000 species of intermediately expressed mRNA comprise 40 to 60 percent of the amount of mRNA, and 10,000 to 20,000 rare species of mRNA comprise less than 20 to 40 percent of the amount of mRNA. This average distribution may vary markedly between tissue sources, and the presence of numerous highly expressed genes may further alter this distribution. Sequencing cDNA from standard cDNA libraries is ineffective to discover rarely expressed genes because intermediately and highly expressed cDNA ends up being excessively sequenced.

Once most mRNAs of the superprelevant and intermediate frequency classes have been identified, redundancy levels are expected to exceed 60 percent. Thus, the use of a hybridization normalization method has been proposed to solve this problem. The principle behind normalization is to decrease the frequency of the most abundant clones while increasing the frequency of less prevalent cDNAs. Several methods of normalization for the preparation of EST cDNAs are introduced by Soares et al., 1994, Proc. Natl. Acad. Sci. 91:9228–9232, who has disclosed a normalization method for preparing EST sequences. This method is based on the reassociation of nucleic acids cloned in amplified plasmid libraries. However, amplified plasmid libraries subjected to normalization are not useful for the preparation of long-strand, full-coding/length cDNAs. This is because there is a cloning bias associated with plasmid libraries where short-strand cDNAs are efficiently cloned with cloning efficiency decreasing with the length of the strand. In fact, in Soares et al., 1994, DNA must be cloned into a plasmid and then be converted to tester single-strand DNA. The ligation to plasmids reduces the strand length of the cDNA that is recovered (that is, long strands of cDNA tend to be lost).

Additionally, during library amplification prior to normalization, the ease with which cDNA clones are grown varies with plasmid length. Thus, long-strand, full-coding/length clones tend to be underrepresented following bulk amplification of the library. In amplified plasmid libraries, the recovery of full-coding/length clones becomes even more difficult.

Other literature, such as Tanaka et al., 1996, Genomics, 35:231–235, discloses methods for the preparation of EST sequences in which mRNA is first annealed on oligo-dT conjugated on a solid matrix. This method is not suitable for preparing normalized long-strand, full-coding/length cDNAs because of mRNA degradation before cDNA synthesis. Further, the hybridization rate of nucleic acids immobilized on a solid phase is slower than that in solution hybridization.

Libraries created with PCR- and solid matrix-based normalization technologies known in the art exhibit sequence redundancy similar to that of non-normalized cDNA libraries used in EST projects.

An additional problem consists in that in the preparation cDNA libraries or encyclopedias (for example, a mammal full-length cDNA encyclopedia) with the aim of collecting at least one long-strand, full-coding/length cDNA for each gene expressed irrespective of the tissue source, not only is it desirable to remove cDNAs that are redundant within the library, but also cDNAs that have already appeared in previous libraries, so as to accelerate the discovery of new long-strand, full-coding/length cDNAs.

To solve this problem, hybridization subtraction methods have been proposed.

Sagerstrom et al., Annu. Rev. Biochem., 1997, 66:751–83, gives an overview of the subtraction methods known in the art. The basic idea of subtraction is that the nucleic acid from which one wants to isolate differentially expressed sequences (the tracer or tester) is hybridized to complementary nucleic acid that is believed to lack sequences of interest (drivers) and in which the drivers are present in much higher concentration than thetesters. The tester and driver nucleic acid populations are allowed to hybridize, with only sequences common to the two populations forming hybrids. After hybridization, driver-tester hybrids and unhybridized drivers are removed, and the remaining nucleic acids can be used to prepare a library rich in tester-specific clones or to make probes that can be used to screen a library for tester-specific clones.

However, subtraction methods also entail the same problems described for normalization with PCR- and solid matrix-based technologies. They are suited to the preparation of EST sequences, but cannot be used to prepare long-strand, full-coding/length cDNAs.

Bonaldo et al., 1996, Genome Reseach, 6:791–806, discloses a subtractive hybridization approach specifically applied to reducing the expression of pools of already sequenced clones from normalized libraries yet to be surveyed.

This normalization and subtraction technique (Bonaldo et al. 1996) is useful for large-scale gene discovery in EST research, but has the drawbacks already indicated in prior art (cDNA cloned in amplified plasmid as disclosed by Soares et al., 1994) and is not suited to long-strand and full-coding/length cDNA inserts.

Inparticular, as stated above, during library amplification prior to the normalization and subtraction steps, the amplification of cDNA clones varies with plasmid length, with long clones being underrepresented following bulk amplification of the library. That is, the relative expression of long-strand cDNA clones decreases, rendering such cloning difficult.

A further problem of the normalization and subtraction method disclosed by Bonaldo et al. is that both the normalization and subtraction steps require incubation and an incubation period causing the breakup of plasmids—bigger plasmids (containing long-strand cDNAs) in particular. As a consequence of the normalization and subtraction steps, the number of resulting long clones is very limited ornull.

This also confirms the unsuitability of this method to the preparation of normalized and subtracted long-strand, full-cloning/length cDNAs.

A still further problem relating to normalization and/or subtraction methods is that non-specifically-bound tester/driver hybrids form in these steps due to complementary binding of imperfect sequences. The removal of such hybrids would result in the elimination from the tester of targeted cDNAs erroneously considered to be abundant and/or to have already been sequenced in other libraries, but which in reality are not abundant and have not been previously sequenced.

Accordingly, the purpose of the present invention is to solve the several problems of prior art and to provide an efficient method for the preparation of normalized and/or subtracted long-strand and full-coding/length cDNA libraries.

SUMMARY OF THE INVENTION

The present invention provides a method capable not only of normalizing cDNA, but also of subtracting cDNAs that have already appeared in other libraries. Accordingly, the present invention provides an efficient method for the preparation of normalized and/or subtracted cDNAs, preferably, long-strand and/or full-coding/length cDNA or cDNA libraries. Based on this method, the problems of PCR- and solid matrix-based techniques are solved.

Accordingly, an embodiment of the present invention relates to a method of preparing normalized and/or subtracted cDNA, characterized in that the normalized and/or substracted cDNA is reverse transcript of mRNA and cDNA that has not been cloned (hereinafter referred to as cDNA tester). This avoids the drawbacks of the state of the art caused by cloned cDNA tester amplified in plasmid.

This method comprising the following steps:
I) preparing uncloned cDNA tester, preferably a cDNA tester not cloned in plasmid;
II) preparing polynucleotide drivers for normalization and/or subtraction;
III) normalizing and/or subtracting (one, two, or more steps), removing the tester/driver hybrids obtained by normalization and/or subtraction, and removing unhybridized polynucleotide drivers; and
IV) recovering the normalized and/or subtracted cDNA.

The DNA tester of step I) is preferably long-strand, full-coding/length cDNA.

Further, the method of the present invention may comprise the step of V) by preparing a second strand cDNA complementary to the normalized and/or subtracted cDNA and cloning the double-strand cDNA that is recovered.

According to another embodiment, the present invention relates to a method of preparing cDNA, preferably long-strand, full-coding/length cDNA, wherein the normalization and subtraction drivers are mixed together and normalization and subtraction are performed in a single step (normalization/subtraction).

According to a further embodiment, a method of improving normalization and/or subtraction by eliminating RNA (driver) bound non-specifically to cDNA (tester) by treating the non-specific binding RNA/DNA hybrid with an enzyme capable of severing single-strand sites in RNA drivers is provided. This enzyme can be a nuclease, in particular, a ribonuclease capable of cleaving single-strand RNA or a mixture thereof. Preferably RNase I (also indicated as RNase 1) can be employed.

However, this treatment is not limited to the normalization and subtraction of hybrids in the method of preparing cDNA, but can be used to cleave sites in RNA that has become partly single-stranded as a result of nonspecific binding and thus selectively remove nonspecifically bound RNA/DNA hybrids in any species of nonspecifically-bound RNA/DNA hybrid.

Accordingly, a method of preparing single-strand and/or double-strand cDNA by treating nonspecifically bound RNA/DNA hybrids with an enzyme capable of cleaving single-strand RNA (capable of cleaving sites in RNA that has become partly single-stranded), removing the cleaved RNA, and recovering the cDNA is provided.

The normalized and/or subtracted cDNA prepared by any of the methods of the present invention may be single-strand or double-strand cDNA.

Figure 1:
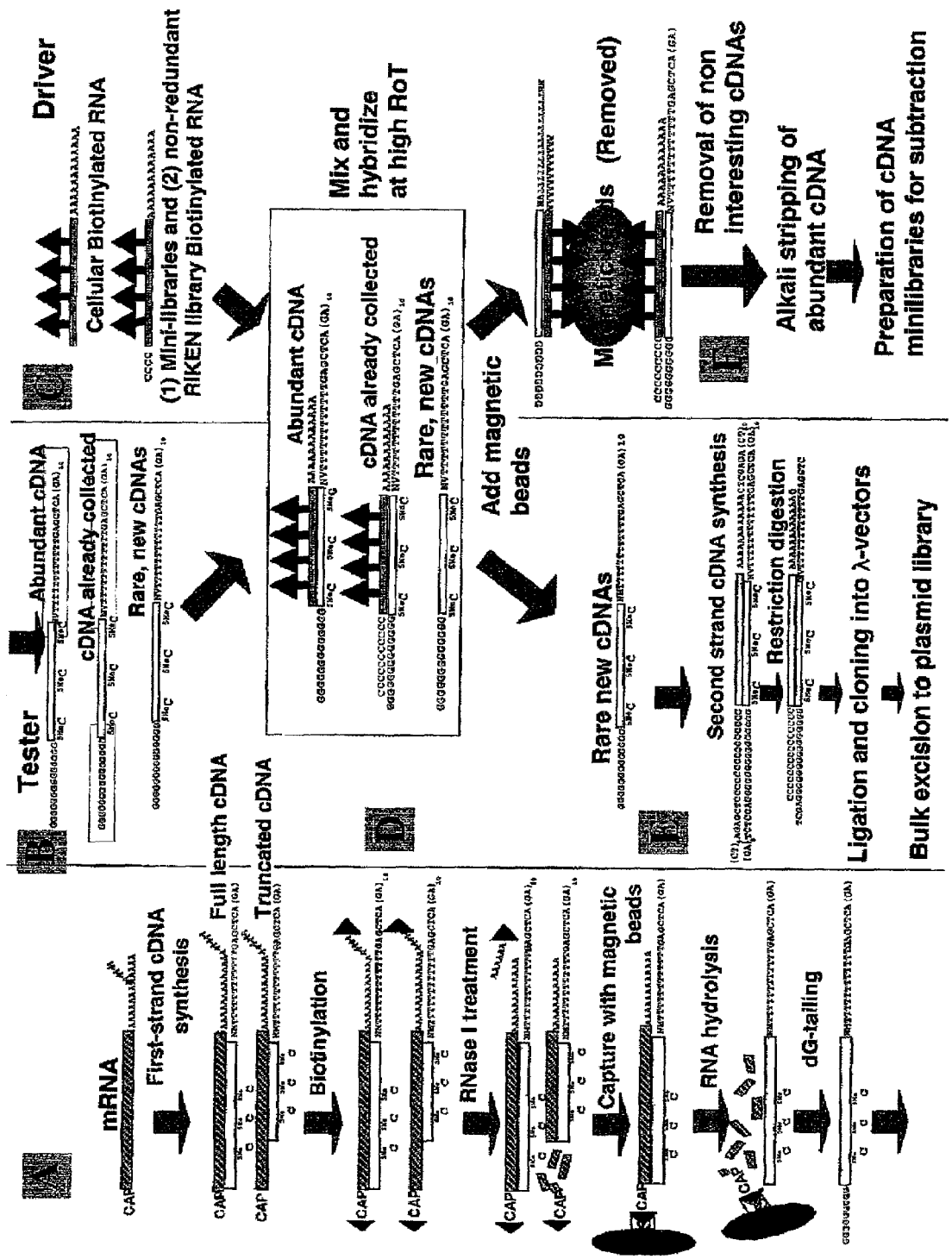
FIG. 1 is a schematic of a suitable normalized and/or subtracted cDNA preparation protocol. A) A general scheme for the preparation of long-strand, full-coding/length single-strand cDNA; B) Representation of a population of different tester cDNAs; C) normalizing drivers (cellular mRNA) and subtracting drivers (run-off transcripts); D) hybridization; E) rare/new cDNAs are used for second strand cDNA preparation (normalized/subtracted cDNA library); F) abundant cDNAs/unwanted cDNAs are removed and may be used for the preparation of minilibraries to implement subtraction.

Only one clone (cDNA) tester was used and it was subtracted with a driver made with the same cDNA.

Lanes 1–3 show subtracted cDNA when biotinylation was performed in ice, and lanes 4–6 when performed at room temperature (RT). Lanes 7–9 comprise tester and driver without bead treatment (therefore not removed) at 100 percent, 10 percent and 2 percent, respectively.

Lane 9 shows that a quantity of 2 percent, even if low, is still evident. In lanes 1–6, there is no evident presence of tester/driver hybrid, indicating that subtraction was almost 100 percent.

DETAILED DESCRIPTION OF THE INVENTION

According to an embodiment of the present invention, an efficient method for the preparation of normalized and/or subtracted cDNA or cDNA libraries, preferably long, and/or full-coding/length cDNA libraries, is provided by preparing uncloned cDNA as tester. The uncloned cDNA tester may be cDNA not cloned in plasmid.

This method does not require the PCR cloning step and the binding of oligo-dT to solid matrix before the normalization and/or subtraction step/s (one, two, or more steps). As a result, long and/or full-coding/length cDNAs are recovered.

Accordingly, the method of the present invention may comprise only the normalization step, only the subtraction step, both the normalization and subtraction steps in any order, or normalization and subtraction performed in a single step.

These normalized and/or subtracted cDNAs are treated to synthesize a complementary second strand when they are single-strand, and finally cloned.

Accordingly, this method comprises the steps of:
I) preparing an uncloned cDNA (tester);
II) preparing polynucleotide (driver) for normalization and/or subtraction;
III) performing the normalization and/or the subtraction step/s (one, two, or more steps), and removing the tester/driver hybrids obtained by normalization and/or subtraction and the non-hybridized polynucleotide drivers; and
IV) recovering normalized and/or subtracted cDNA (rare and/or new cDNAs).

The method based on the present invention further comprises, when the cDNA tester is single-strand, a step V): preparing the second cDNA strand and cloning.

The above steps I)–V) can be repeated several times (two-times, three-times, etc.) according to the convenience.

The uncloned cDNA tester of step I) may be cDNA not cloned in plasmid. The cDNA tester of step I) may be a reverse transcript of mRNA in the form of an uncloned cDNA. The uncloned cDNA of step I) is preferable a long and/or full-coding/length cDNA tester.

For the purposes of the present invention, the term "full-length cDNA" is used to denote 5' and 3' UTR sequences and T-primer oligonucleotides (that are complementary to mRNA comprising poly-A). "Full-coding cDNA" means a cDNA sequence comprising at least a start codon and a stop codon. And by "long-strand cDNA" is understood a cDNA sequence which is almost full-coding and/or full-length but lacks one or more bases at the 3' end (corresponding to the 5' end of mRNA) or at the 5' end if considering a cDNA strand complementary to cDNA that is complementary to mRNA (that is, cDNA having the same direction as the gene). This early stop (before reaching the 5' end) can be caused by the formation of a secondary structure in the mRNA at the Cap structure level, impeding synthesis of cDNA.

The cDNA tester according to the invention may be a single or double strand. In case of double strand, it is treated according to the technique known in the art allowing dissociation of double strand cDNA in single strand and, in presence of RNA driver, allowing the formation of hybrid cDNA/RNA. An example of this technique comprises mixing the tester double strand cDNA and RNA driver in presence of formamide at a concentration higher than 50%, preferably 80%, at temperature 40–60° C., preferably 50° C., in usual hybridization buffer).

The cDNA tester of step I) can be prepared by any method of cDNA preparation known in prior art, preferably any known method for the preparation of long-strand and/or full-coding and full-length cDNAs. Examples are Ederly et al.; Kato et al.; and Maruyama et al.(the oligo-capping method).

In particular, the oligo-capping method is a method where phosphoric esters of incomplete cDNAs without 5' Caps are removed with alkaline phosphatase and then all cDNAs are treated with the tobacco acid pyrophosphatase (TAP) used as decapping enzyme so that only full-length cDNAs have phosphates.

Preferably, a method employing the CAP-trapping technique described by Carninci et al., 1996, Genomics 37:327–336, and Carninci and Hayashizaki, 1999, Methods Enzymol, 303: 1–44, is used.

An example of this method is schematically illustrated in section A of FIG. 1.

mRNA is isolated from tissue and RNA-DNA hybrids are made by reverse transcriptase starting from primers such as oligo-dT or random or specific primer-adapters, using mRNA as template. A tag molecule is then chemically bound to the diol structure of the 5' CAP ($^{7Me}G_{ppp}N$) site of the mRNA forming the hybrid. Finally, RNA-DNA hybrids carrying a DNA corresponding to long, full-coding/length mRNA are separated from hybrids carrying tag molecules by binding the tag molecules.

Tag molecules that are bound to the Cap after formation of the RNA-DNA hybrids are particularly advantageous because the hybrid structure of RNA-DNA can escape chemical cleavage of mRNA during the aldehydration of the diol structure necessary for labelling mRNAs with tag molecules. As a result, the efficiency of full-coding/length cDNA synthesis increases.

The tag molecule can be bound to the 5' Cap site by, for example, an oxidation ring-opening reaction of the 5' Cap site diol structure with an oxidizing agent such as sodium periodate to form a dialdehyde and subsequent reaction of the dialdehyde with a tag molecule having a hydrazine terminal.

Examples of tag molecules having hydrazine terminals are biotin, avidin and streptavidin, as well as digoxigenin molecules having hydrazine terminals. A molecule showing reaction specificity, such as antigens and antibodies, can also be used as tag molecule. The label molecule employed as tag molecule is not specifically limited.

Accordingly, the preparation of cDNA used to practice any of the methods based on the present invention comprises the steps of:
(1) synthesizing a first strand of cDNA by reverse transcriptase forming the hybrid mRNA/cDNA;
(2) chemically binding a tag molecule to the diol structure of the 5' CAP ($^{7Me}G_{ppp}N$) site of the mRNA forming the hybrid;
(3) capturing long, full-coding, and full-length cDNA hybrids; and
(4) removing single-strand mRNA by digestion with an enzyme (preferably with RNase H) that is capable of cleaving single strand mRNA or by using an alkali (preferably NaOH).

A more specific example of a method for preparing cDNA including steps from (1) synthesizing first cDNA strands to (7) synthesizing double-stranded full-coding/length cDNA (having for example biotin as tag molecule) is as follows:
(1) synthesis of first strand cDNA (synthesis of an RNA-DNA hybrid);
(2) biotinylation of an mRNA of the RNA-DNA hybrid;
(3) ribonuclease I (RNase I) digestion;
(4) capture of a full-coding/length cDNA hybrid (with avidin or streptavidin beads);
(5) removal of hybrid RNA (RNase H digestion);
(6) G tail addition by terminal deoxynucleotidyl transferase; and
(7) preparation of second strand (double stranded full-coding/length cDNA) primed with oligo C.

Alternatively, step (5) can be performed with an alkali (preferably NaOH). The cDNA prepared in step (6) may be used as cDNA tester for the purpose of the present invention. After normalization and/or subtraction, step (7) may be performed. The cDNA obtained by the method of step I) consists of various populations of cDNA, namely superprevalent (or highly expressed or class I), intermediate (or class II) and rare cDNAs (class III) as indicated in section B of FIG. 1 (intermediate and superprevalent are indicated together in section B as abundant). Some of these cDNAs must be considered as having been previously collected in other libraries and are indicated in section B as previously collected cDNA. The cDNAs that were obtained are indicated in section B as "testers".

In step II), "drivers" are prepared for normalization and/or subtraction.

Normalization drivers are RNA or DNA obtained from the same tissue as the population, and/or the same population, that one intends to eliminate.

Normalization drivers can be for example cellular mRNAs of the same library, that is, aliquots of the mRNAs initially used to prepare the cDNA library (starting material mRNA). Normalization drivers can also be cDNA obtained from the same library that one intends to normalize. In that case, single-strand cDNAs have to be prepared from the cDNA library by PCR, for example.

Subtraction drivers are RNA or DNA obtained from different tissue from that which one intends to substract, RNA or DNA obtained from the same or a different strain (system) from that which one intends to subtract, or the same tissue belonging to a different population from the population that one intends to eliminate.

In vitro-transcribed RNA from a DNA library, preferably clones from different tissue or from the same tissue but belonging to a different population and prepared with the cap-trapper technology, can be employed in the subtraction step. However, subtraction drivers prepared with any method known in the art, for example, as described by Sagerstrom et al., 1997, Annu. Rev. Biochem., 66:751–83, can be used for the purpose of the present invention.

For example, subtraction drivers can be run-off transcripts from minilibraries containing expressed genes, rearrayed clones, and in some cases, previously sequenced (but not necessarily) cDNAs.

Subtraction run-off transcripts are obtained by RNA polymerase (for example, T7, T3, SP6 or K11 RNA polymerase) from DNA templates carrying appropriate promoters, such as a DNA sequence flanked with promoters, plasmids, phages, and analogs thereof. In the case of plasmids, subtraction transcripts can be prepared by amplifying the cDNA library or rearrayed library with a solid or liquid phase. Preferably, subtraction transcripts can be prepared by spotting colonies obtained from well plates (for example 384 well plates) onto LB+ ampicillin-agar plates, growing them at a temperature of from 30° C. to 37° C., and following overnight growth, scraping the colonies for use in bulk plasmid preparation.

DNA can also be used for subtraction drivers. In that case, single-strand DNA isolated from clones obtained from different tissues or from the same tissue but belonging to a different DNA population can be used.

Minilibraries are libraries comprising a portion of the clones of the starting tissue or of different tissues.

A schematic example of the preparation of drivers for normalization and/or for subtraction is shown in section C of FIG. 1. However, methods based on the present invention comprise only the normalization step, only the subtraction step, the normalization and subtraction steps in any order, or normalization/subtraction in a single step. These drivers can be bound with a tag molecule. This (first) tag molecule can be any molecule able to bind or tag the drivers and also able to bind to a matrix permitting elimination of the driver. The tag molecule can also bind a second tag molecule, which can be the same as the first tag molecule or a different molecule, this second tag molecule being able to bind to a matrix or to a further tag molecule. Preferred tag molecules are biotin, avidin, strepavidin, digoxigenin, or any antibody thereto, preferably an antibiotin, antiavidin, antistrepavidin or or antidigoxigenin antibody, or any antiantigen antibody thereof. However, the tag molecule is not limited to these substances.

Steps III) and IV) can be executed in different order depending on whether the normalization and subtraction steps are carried out consecutively or in a single step.

According to a first approach, normalization step (III) is performed by mixing with normalization drivers, followed by elimination of the hybrids and recovery of the normalized single-strand cDNAs (step IV). Next, these single-strand cDNAs are mixed with subtractive drivers (step III), the hybrids are eliminated and (normalized and) subtracted single strand cDNAs are recovered (step IV). The single-strand cDNAs that are recovered consist of rare and new cDNAs as exemplified in section D of FIG. 1. The normalization and subtraction steps can also be performed in inverted order.

According to another approach, the normalization drivers and the subtractive drivers prepared in step II) are mixed together, with a single normalization/subtraction step being performed in step III).

The implementation of normalization/substraction in a single step affords the advantage of performing only one incubation step (instead of two). Performing the normalization and subtraction in two different distinct steps entails the problem of performing two incubation steps and each incubation step tends to reduce the number of long and/or full-coding/length cDNAs. Thus, performing only a single incubation step is advantageous.

However, the normalization and/or subtraction step and the single normalization/subtraction step can be repeated, if necessary, before final recovery of the rare new cDNAs and synthesis of second strand cDNA.

Accordingly, the present invention also discloses a method for the preparation of normalized and subtracted cDNA comprising the steps of I) preparing a cDNA tester, which may be uncloned according to the first embodiment above but not limited to it, II) preparing polynucleotide normalization driver and polynucleotide subtraction driver (normalization/subtraction drivers), III) performing normalization and subtraction in one single step, by mixing together the tester and the normalization/subtraction drivers, and IV) recovering the normalized and subtracted cDNA.

This method may also include the step of adding an enzyme capable of cleaving single-stranded RNA driver nonspecifically bound to single strand, for example using RNase I, and removing the cleaved single strand RNA driver. This step of addition of RNase I or other enzyme capable of cleaving single-stranded RNA is disclosed more in details later.

The preparation of normalization and/or subtractive drivers, the hybridization step(s) (one or more), and the removal of "uninteresting cDNAs", i.e. hybrids produced in the normalization and/or subtraction steps and single drivers (drivers not forming hybrids) can be accomplished by any technique known to the art. For example, these may be conducted as described in Bonaldo et al., 1996, and in Sagerstrom et al. 1997, Annu. Rev. Biochem., 66:751–783 (from page 765; also Table 1).

As a specific example, the hybridization technique relating to photoactivated biotin, strepavidin binding and organic extraction described by Barr F. G. and Beverly S. Emanuel, 1990, Analytical Biochemistry, 186: 369–373 or in Hazel L. Sive and Tom St John, 1988, Nucleic Acids Research, Vol. 16, number 22, from page 10,937, can be employed.

However, techniques known in the art such as are described by Sagerstrom et al., 1997, may be employed.

Following normalization and/or subtraction the tester/driver hybrids are removed by any technique known in the art, such as that described by Sagerstrom et al., 1997, from page 765. For example, this may be accomplished by the addition of a matrix such as beads, preferably magnetic beads or agarose beads. The beads are preferably covered with a tag molecule, as set for above, or bind to tag molecules. Beads covered with streptavidin (generally referred to as "streptavidin beads") are preferred, with magnetic porous glass (MPG) streptavidin beads (CPG Inc.) being even more preferred. Beads covered with or bonded to avidin, biotin, digoxigenin, an antibody, or an antigen can also be used. The antibody covering or bound to the beads (one, two, or more types of beads) can be an antibody generally able to recognize tag molecules, preferably an antibody which recognizes antibody bound to the drivers, or an antibiotin antibody, antiavidin antibody, antistreptavidin antibody, or antidigoxigenin antibody which recognizes biotin, avidin, streptavidin or digoxigenin bound to the drivers.

An example of magnetic beads bound to or covered with biotin as a tag molecule forming a tester/driver hybrid-bead aggregate is shown in section F of FIG. 1.

Streptavidin or avidin/phenol may be employed instead of magnetic beads to remove the hybrid (Sive H. L. and St. John T., 1988, Nucleic Acids Res., 16:10937; and Sagerstrom et al., 1997).

It is also possible to employ hydroxyapatite (HAP) and unlabeled RNA to remove tester/driver hybrids. An example is described by Sagerstrom et al., page 765 and Table 1.

Figure 6:
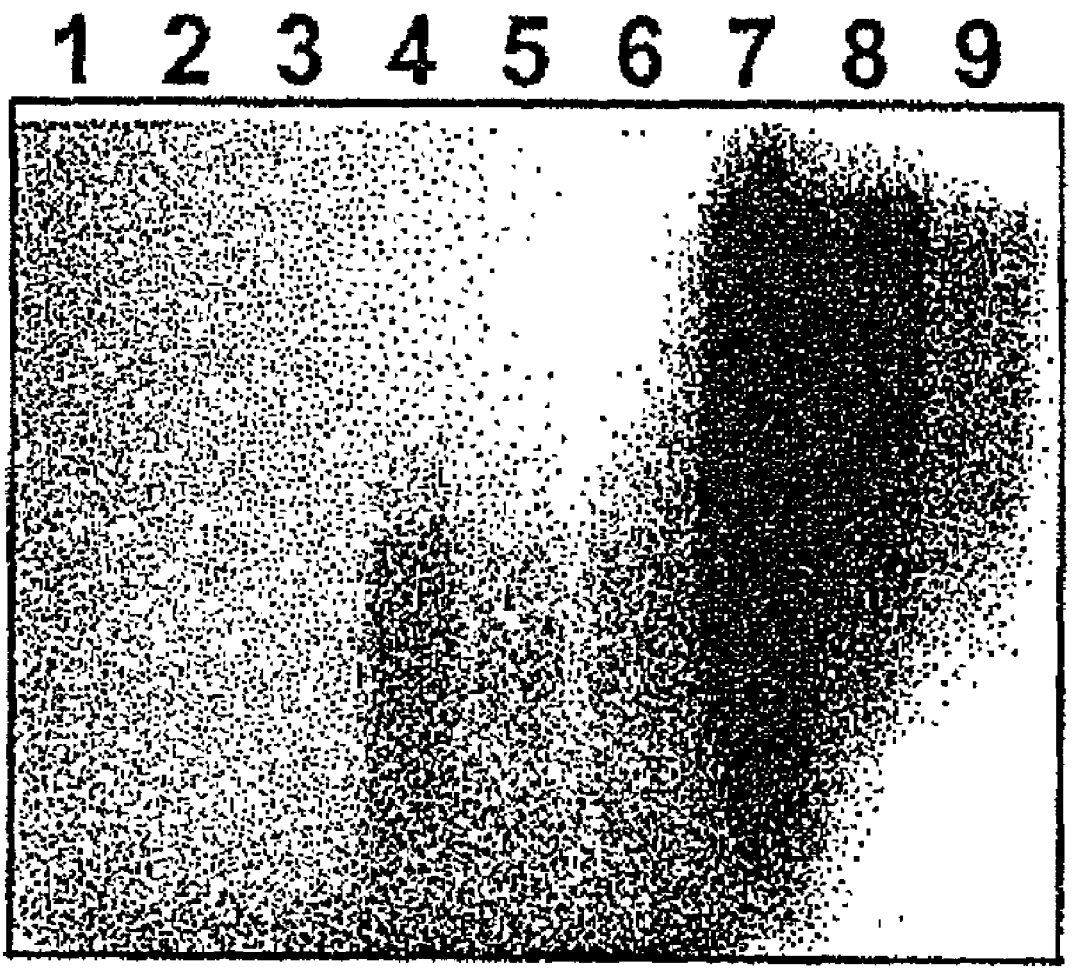
FIG. 6 shows an electrophoresis test for evaluating the efficiency of removal of driver/tester captured using a subtraction method based on the present invention.

The removal of tester/driver hybrids by the subtraction method based on the present invention permits almost 100 percent removal as seen from the electrophoresis of FIG. 6 and from Example 3.

The cDNA of the removed tester/driver hybrids can be used for the preparation of cDNA minilibraries to be used for further subtractions steps as shown in section F of FIG. 1.

The normalized and subtracted cDNAs (rare and new cDNAs) that are recovered in step IV) are then treated to synthesize second cDNA strands, subjected to restriction digestion, ligated, and cloned into vectors, as schematically indicated in section E of FIG. 1.

The advantage of the method based on the present invention is that it maintains a high proportion of long, full-coding/length cDNAs in the subtracted/normalized library. Further, the present method increases the discovery of new genes relative to the results obtained by using standard, full-length cDNA libraries prepared based on prior art.

That is, in the method of the present invention, normalized and/or substracted cDNA (tester cDNA) is an uncloned cDNA. Preferably, a cDNA not cloned in a plasmid. Preferably, the tester acccording to the invention is a reverse transcript of mRNA in the form of uncloned cDNA. This cDNA is preferably a single-strand. Thus, the prior art problem of cloning bias against large cDNAs in plasmid libraries and the problem in libraries generated by normalization techniques based on PCR and solid matrixes can be avoided, and the advantage of increased discovery of new genes is afforded.

As stated in the prior art section, a further problem relating to normalization and/or subtraction methods is that non-specific tester/driver hybrids form during these steps due to complementarity binding of imperfect sequences. For example, this is caused by cross-reactivity between similar but unidentical sequences in testers and drivers. The removal of such hybrids eliminates from the tester cDNAs those cDNAs considered to be erroneously abundant and/or to have been already sequenced in other libraries, as well as other desirable sequences. This constitutes a major drawback to normalized/subtracted libraries.

Figure 2:
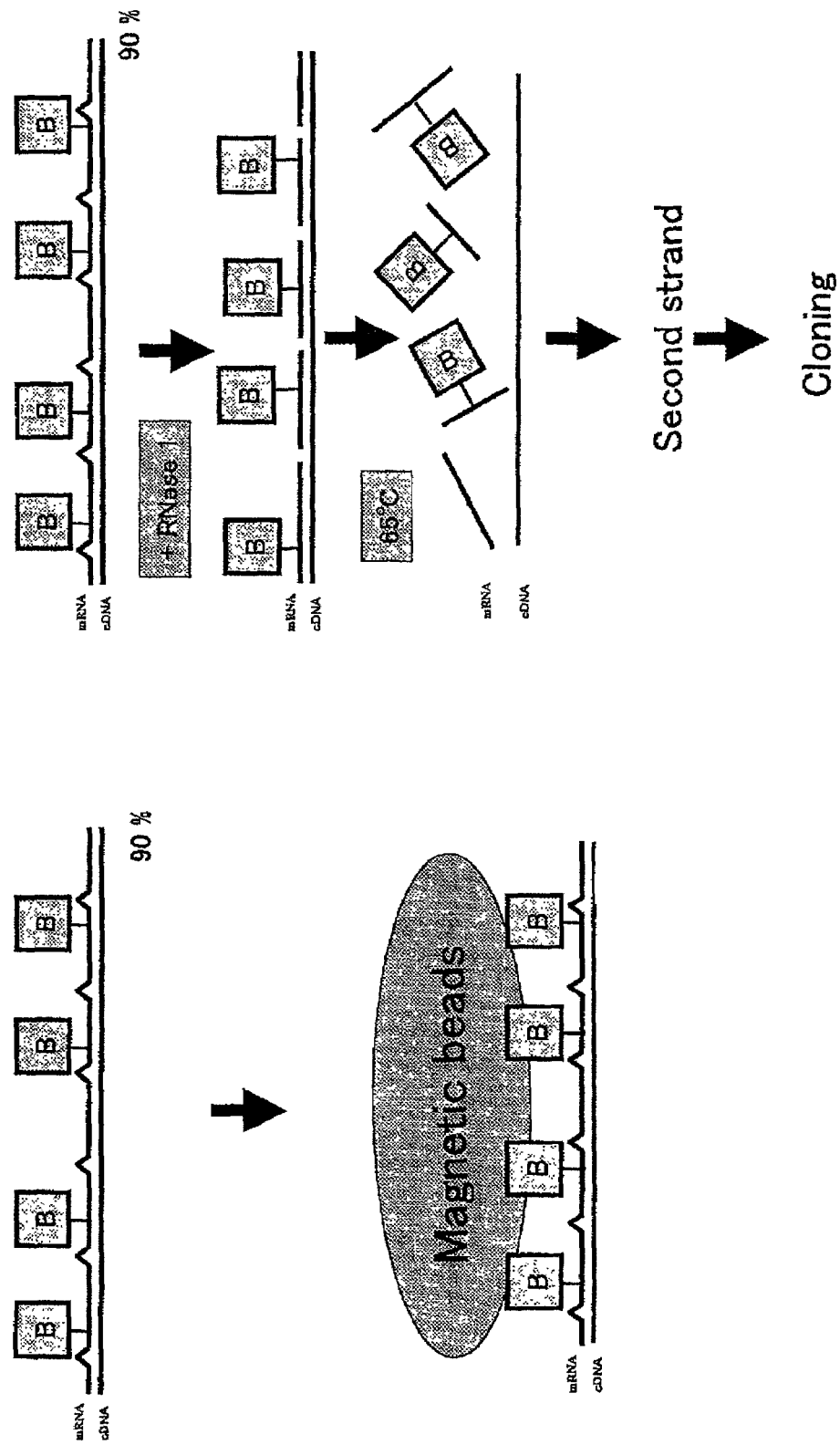
FIG. 2 shows (on the right side of the drawing) the use of RNase I able to recognize and cleave RNA (driver) bound non-specifically to cDNA (tester). With this method, new and/or rare cDNAs are recovered. In contrast, as shown on the left side of the figure, when no RNase I treatment is performed, the new and/or rare tester bound non-specifically to the driver is captured by beads and removed.

This problem is schematically depicted in FIG. 2. On the left side of FIG. 2, normalization and/or subtractive drivers (mRNA, upper strands) are non-specifically bound (there is a portion of the mRNA that is not bound to the cDNA) to cDNAs (lower strands) that are new and/or rare but erroneously believed to be abundant and/or to have been previously collected. cDNA testers that are bound to drivers, albeit nonspecifically, are removed during normalization and/or subtraction as indicated in FIG. 1. Thus, when the cDNA testers are new and/or rare cDNAs, they are lost.

In the method of the present invention, in such nonspecific binding, such as is shown on the right side of FIG. 2, drivers that are nonspecifically bound to cDNA testers are eliminated by degrading RNA with RNase I or some other enzyme described further below and the new and/or rare cDNA is recovered.

As shown in FIG. 2, one embodiment of the present invention provides a method in which nonspecifically binding RNA/DNA hybrids are processed (digested) by an enzyme cleaving single-strand RNA (an enzyme having the ability to cleave single-strand sites in RNA drivers nonspecifically bound to cDNA testers) to cleave single-strand sites of RNA (drivers) nonspecifically bound to cDNA (testers). Next, hybrids with RNA that has been cleaved from the cDNA testers are eliminated (denatured) to remove the cleaved RNA from the system, leaving the cDNA testers and improving the efficiency of normalization and subtraction (that is, reducing unintended exclusion from the rare cDNA system).

There is no limitation to the method of removing RNA fragments from the nonspecifically bound RNA/DNA hybrids that have been treated with enzymes cleaving single-strand RNA. For example, as shown in FIG. 2, the hybrids may be processed at a suitable temperature to eliminate, that is, denature, hybrids with RNA that has been cleaved from cDNA tester, and the RNA freed from the cDNA tester may be removed using tags bound to the RNA, for example. The elimination of hybrids with RNA that has been cleaved from cDNA tester does not affect specifically bound RNA/DNA hybrids. The conditions for selectively denaturing hybrids that have been cleaved and the strand length of the hybrid portion that has been shortened are suitably selected. Denaturing conditions depend not just on temperature, but also on the pH of the system (the aqueous solution containing the hybrids), salt concentrations, and the like. Denaturing is conducted for example by processing at a temperature of 25–100° C. (i.e. up to the boiling point), preferably 37–70° C., and still more preferably at a temperature of 65° C. The use of the above-stated temperature denatures hybrids of partially cleaved RNA, the RNA previously comprising the hybrids dissociates from the cDNA, the dissociated RNA is bound to beads using tags bound to the RNA, and the RNA fragments bound to the beads are removed with a magnet by the usual methods. Specifically bound RNA/DNA hybrids are maintained under the above-stated denaturing conditions, and tags bound to the RNA in the same manner as set forth above may be used for binding to beads and removal. That is, conventional normalization and/or subtraction are employed.

A single-strand-specific RNA endonuclease (ribonuclease) can be employed as the above-described enzme cleaving single-strand RNA. Examples suitable for use are RNaseA specific to pyrimidine (U and C), RNase 4 specific to U, RNase T1 specific to G, RNase 2 or RNase 3 specific to U, and RNase I able to degrade any ribonucleoside (Hyone-Myong Eun, Chapter for "Nucleases"; Sorrentino Salvatore and Libonati Massimo, 1997, FEBS Letters, 404: 1–5: these authors use the arabic numbers in order to indicate the above ribonucleases, however these ribonucleases are also indicated with the roman numbers in literature). Alternatively, RNase T2 having little base specificity can be used as the enzyme cleaving single-strand RNA (BioTechniques, 232, Vol.12, No.2, 1992).

RNase I is employed with preference as the enzyme cleaving single-strand RNA. A mixture of the above-listed ribonucleases may also be employed. Hybrids may be subjected to the action of single-strand-specific RNA endonucleases by the usual methods. For example, 0.01–1 unit of a single-strand-specific RNA endonuclease may be employed per 1 µg of driver.

The step of degrading mRNA drivers nonspecifically bound to cDNA testers may be conducted in the normalization/subtraction step based on the present invention, following the normalization and/or substraction step, or after a single normalization/substraction step.

The cDNA tester according to this method can be cloned or uncloned cDNA. Uncloned tester can be for example a cDNA not cloned in plasmid. The cDNA tester is preferably a reverse transcript of mRNA in form of uncloned cDNA.

The cDNA tester is preferably a long-strand, full-coding, and/or full-length cDNA, preferably prepared according to the cap-trapping technology as above described.

Accordingly, an aspect of the of the present invention is a method specifically comprising the steps of:
 (a) preparing cDNA testers;
 (b) preparing normalization and/or subtraction RNA drivers;
 (c) performing normalization and/or subtraction in two steps in any order, or performing normalization/subtraction in a single step by mixing normalization/subtraction RNA drivers with cDNA testers;
 (d) adding an enzyme having the ability to cleave single strand sites on RNA drivers nonspecifically bound to cDNA testers;
 (e) removing the cleaved single-strand RNA drivers of step d) from the testers and removing tester/driver hybrids;
 (f) recovering normalized and/or subtracted cDNAs; and
 (g) preparing second strand cDNAs and cloning the recovered cDNAs.

The processing methods for removing single-strand RNA drivers can be applied beyond the normalization and substraction of hybrids in methods of preparing cDNA. For example, they can be used to remove partially single-strand RNA in all types of nonspecific RNA/DNA hybrids.

That is, the present invention comprises a method of treating nonspecifically bound RNA/DNA hybrids with an enzyme capable of degrading single-strand RNA to remove RNA that is nonspecifically bound to DNA. In this method, nonspecifically bound RNA/DNA hybrids are treated with an enzyme capable of degrading single-strand RNA to degrade RNA nonspecifically bound to DNA and remove it from mixtures of DNA and/or RNA/DNA hybrids specifically bound to DNA. This method may be employed with the object of recovering DNA nonspecifically bound to RNA or with the object of recovering just DNA hybrids specifically bound to RNA.

In the present method, as set forth above, the enzyme capable of degrading single-strand RNA may either be selected from the group consisting of RNase I, RNaseA, RNase4, RNaseT1, RNaseT2, RNase2, and RNase 3, or comprise a mixture thereof. RNase I is the enzyme of preference.

The RNA/DNA hybrids including the above-described nonspecifically bound RNA/DNA hybrids may be the products of methods comprising normalization and subtraction steps conducted in any order or the products of methods comprising a single step of normalization/subtraction. That is, nonspecifically bound RNA/DNA hybrids may be removed from RNA/DNA hybrids obtained by conventional normalization and/or subtraction methods and the recovery rate of long-strand or rare cDNA improved. Accordingly, the cDNA forming the above-described nonspecifically bound RNA/DNA hybrids can be long-strand, full-coding and/or full-length cDNA.

The present invention further discloses a method of isolating single-strand cDNA in which the above-described hybrids comprising RNA nonspecifically bound to cDNA is treated with an enzyme capable of degrading single-strand RNA, the degraded single-strand RNA is removed, and the DNA is recovered. In this method, the (degraded) single-strand RNA that is produced by treatment with an enzyme capable of degrading single-strand RNA is removed from the system comprising the hybrids, resulting in the recovery of single-strand cDNA. Based on this method, cDNA nonspecifically bound to certain RNA may be selectively recovered.

In this method, in the same manner as above, the enzyme capable of degrading single-strand RNA is either selected from among the group consisting of RNase I, RNaseA, RNase4, RNaseT1, RNaseT2, RNase2, and RNase3, or is a mixture thereof, with RNase I being preferred. Further, the cDNA may be long-strand, full-coding, and/or full-length DNA.

The present invention further comprises a method of preparing normalized and/or subtracted cDNA in which an enzyme capable of degrading single-strand RNA driver nonspecifically bound to cDNA tester is added and the degraded single-strand RNA driver is removed. In this method, cDNA tester and hybrids comprising single-strand RNA driver nonspecifically bound to the cDNA tester are subjected to the action of an enzyme capable of degrading single-strand RNA driver, and following degradation, the degraded single-strand RNA driver is removed from the system comprising the hybrids.

In this method, in the same manner as above, the enzyme capable of degrading single-strand RNA is either selected from among the group consisting of RNase I, RNaseA, RNase4, RNaseT1, RNaseT2, RNase2, and RNase3, or is a mixture thereof, with RNase I being preferred. Further, the cDNA may be long-strand, full-coding, and/or full-length DNA.

The method of the present invention may be employed to prepare one, two, or more cDNA libraries. The present invention also covers the cDNA and cDNA libraries obtained by the methods of the present invention.

Finally, the methods according to the present invention permit the following:
(i) high-efficiency removal of mRNA drivers;
(ii) no relevant cDNA size reduction following hybridization that would affect the frequency of long, full-coding/length cDNAs;
(iii) suitability to both normalization and subtraction;
(iv) low cross-reactivity between similar but unidentical sequences; and
(v) high-level performance, reproducibility, and ease of handling in terms of both the size of the drivers prepared and the number of libraries.

The methods and embodiments of the present invention will be further described with reference to the following examples.

EXAMPLE 1

Preparation of RNA

Slices of brain tissue (0.5–1 g) (or other tissues as described in Example 2) were homogenized in 10 mL of solution D (Chomczynski , P. and Sacchi, N., 1987, Annal. Biochem., 162:156–159) and extracted with 1 mL of 2M sodium acetate (pH 4.0) and the same amount of a mixture of phenol/chloroform (volume ratio 5:1). After extraction, the same volume of isopropanol was added to the aqueous phase to precipitate RNA. This sample was incubated on ice for an hour and centrifuged at 4000 rpm for 15 minutes with cooling to collect the precipitates. The precipitates were washed with 70 percent ethanol and dissolved in 8 mL of water. A 2 mL quantity of 5M NaCl and 16 mL of an aqueous solution (pH 7.0) comprising 1 percent CTAB (cetyltrimethylammonium bromide), 4M urea, and 50 mM Tris were added to precipitate RNA and the polysaccharides were removed (CTAB precipitate). After centrifugation at 4,000 rpm for 15 minutes at room temperature, the RNA that had been obtained was dissolved in 4 mL of 7M guanidine-Cl. Double the quantity of ethanol was then added to the solution and the mixture was incubated for an hour on ice and centrifuged at 4,000 rpm for 15 minutes. The resulting precipitates were washed with 70 percent ethanol and collected. The precipitates were again dissolved in water and the purity of the RNA was determined by measuring the OD ratio 260/280 (>1.8) and 230/260 (<0.45).

Synthesis of cDNA

From 5 to 10 µg of this RNA, 5 µg of first-strand primer containing the BamHI and SstI restriction sites (5'-(GA)$_5$AGGATCCAAGAGCTC(T)$_{16}$VN-3') (SEQ ID NO:1), and 11.2 µL of 80 percent glycerol were combined to a total volume of 24 µL. The RNA-primer mixture was denatured at 65° C. for 10 min. Simultaneously, 18.2 µL of 5× first-strand synthesis buffer, 9.1 µL of 0.1 M DTT, 6.0 µL (each) of 10 mM dTTP, dGTP, dATP, and 5-methyl-dCTP (instead of dCTP), 29.6 µL of saturated trehalose (approximately 80 percent, low metal content; Fluka Biochemika), and 10.0 µL of Superscript II reverse transcriptase (200 U/µL) were combined to a final volume of 76 µL. A 1.0 µL quantity of [alpha-$^{32}$P]dGTP was placed in a third tube. The mRNA, glycerol, and primers were mixed on ice with the solution containing the Superscript II, and an aliquot (20 percent) was quickly added to the tube containing the [alpha-$^{32}$P]dGTP. First-strand cDNA synthesis was performed in a thermocycler with a heated lid (e.g., MJ Research) according to the following program: step 1, 45° C. for 2 min; step 2, gradient annealing: cooling to 35° C. over 1 min; step 3, complete annealing: 35° C. for 2 min; step 4, 50° C. for 5 min; step 5, increase to 60° C. at 0.1° C. per second; step 6, 55° C. for 2 min; step 7, 60° C. for 2 min; step 8, return to step 6 and repeat for 10 additional cycles. Incorporation of radioactivity permitted estimation of the yield of cDNA (Carninci and Hayashizaki, 1999). The cDNA obtained was treated with proteinase K, extracted with phenol/chloroform and chloroform, and ethanol-precipitated using ammonium acetate as the salt (Carninci and Hayashizaki, 1999).

Biotinylation of mRNA

Before biotinylation, the diol group of the cap and 3'-end of the mRNA was oxidized in a final volume of 50 µL of suspended mRNA/first-strand cDNA hybrid, 66 mM sodium acetate (pH 4.5), and 5 mM NaIO$_4$. Samples were incubated on ice in the dark for 45 min. mRNA/cDNA hybrids were then precipitated by adding 0.5 µL of 10 percent SDS, 11 µL of 5M NaCl, and 61 µL of isopropanol. After incubation in the dark on ice for 45 min or at −20° C. or −80° C. for 30 min, the samples were centrifuged for 10 min at 15,000 rpm. Finally mRNA/cDNA hybrids were rinsed twice with 70 percent ethanol and resuspended in 50 µL of water. The cap was then biotinylated in a final volume of 210 µL by adding 5 µL of 1M sodium acetate (pH 6.1), 5 µL of 10 percent SDS, and 150 µL of 10 mM biotin hydrazide long-arm (Vector Biosystem).

Following overnight (10 to 16 hours) incubation at room temperature (22 to 26° C.), the mRNA/cDNA hybrids were precipitated by adding 75 µL of 1M sodium acetate (pH 6.1), 5 µL of 5M NaCl, and 750 µL of absolute ethanol and incubated on ice for 1 hour or at −20 to −80° C. for 30 min. The mRNA/cDNA hybrids were pelleted by centrifugation at 15,000 rpm for 10 min and the pellet was washed once with 70 percent ethanol and once with 80 percent ethanol. The mRNA/cDNA hybrids were resuspended in 70 µL of 0.1×TE (1 mM Tris [pH 7.5], 0.1 mM EDTA).

Capture and Release of Full-Length cDNA

A 500 µL quantity of MPG-streptavidin beads and 100 µg of DNA-free tRNA were combined and the mixture was incubated on ice for 30 min with occasional stirring. The beads were separated using a magnetic stand for 3 minutes and the supernatant was removed. The beads were then washed three times with 500 µL of washing/binding solution (2 M NaCl, 50 mM EDTA, pH 8.0).

At the same time, 1 unit of RNase I (Promega) was added per µg of starting mRNA to the mRNA/cDNA hybrid sample in buffer supplied by the manufacturer (final volume 200 µL) and the sample was incubated at 37° C. for 15 min. To stop the reaction, the sample was placed on ice and 100 µg of tRNA and 100 µL of 5M NaCl were added. To capture full-coding/length mRNA/cDNA hybrids, the biotinylated, RNase I-treated mRNA/cDNA and the washed beads were combined and resuspended in 400 µL of the washing/binding solution. After mixing, the tube was gently rotated for 30 min at room temperature. The full-coding/length cDNA remained on the beads, and the shortened cDNAs did not. The beads were separated from the supernatant on a magnetic stirrer. The beads were gently washed to remove nonspecifically adsorbed cDNA: two washes with washing/binding solution; one with 0.4 percent SDS and 50 µg/mL tRNA; one with 10 mM Tris-HCl (pH 7.5), 0.2 mM EDTA, 40 µg/mL tRNA, 10 mM NaCl, and 20 percent glycerol; and one with 50 µg/mL tRNA in water.

The cDNA was released from the beads by adding 50 µL of 50 mM NaOH and 5 mM EDTA and incubating for 10 min at room temperature with occasional mixing. The beads then were removed magnetically, and the extracted cDNA was transferred on ice to a tube containing 50 µL of 1M Tris-HCl, pH 7.5. The dissolution cycle was repeated once or twice with 50 µL aliquots of 50 mM NaOH and 5 mM EDTA until most of the cDNA (80 to 90 percent, as measured by monitoring the radioactivity with a hand-held monitor) had been recovered from the beads.

To remove traces of RNA that could later interfere with the biotinylated RNA driver, 100 µL of 1 M Tris-HCl, pH 7.0, and 1 µL of RNase I (10 U/µL) were quickly added to the recovered cDNA on ice; the sample then was incubated at 37° C. for 10 min. The cDNA was treated with proteinase K, phenol/chloroform-extracted, and back-extracted. Two to three µg of glycogen were then added and the sample precipitated from ethanol in a siliconized tube. Alternatively the sample was concentrated by one round of ultrafiltration with a Microcon 100 (Millipore) for 40–60 min at 2,000 rpm. When precipitated from ethanol, the cDNA could be redissolved in 20 µL of 0.1×TE.

In this experiment, RNase H digestion was not conducted. However, hydrolysis was conducted with NaOH, which is capable of simultaneously hydrolyzing and denaturing double strands.

CL-4B Spin-Column Filtration of cDNA

The cDNA samples were treated by CL-4B chromatography (Carninci and Hayashizaki, 1999) or on an S-400 spin column (Amersham-Pharmacia) essentially as described by the manufacturer.

Oligo-dG Tailing of First-Strand cDNA

The cDNA sample, 5 µL of 0×TdT buffer (2 M potassium cacodylate [pH 7.2], 10 mM $MgCl_2$, 10 mM 2-mercaptoethanol), 5 µL of 50 µM dGTP, 5 µL of 10 mM $CoCl_2$, and 40 U terminal deoxynucleotidyl transferase were admixed to a final volume of 50 µL. Samples were incubated at 37° C. for 30 min. At the end, the reaction was stopped with EDTA 20 mM. The cDNA was treated with proteinase K, extracted with phenol chloroform, and precipitated in ethanol. The sample was finally redissolved in TE (10 mM Tris pH 7.5–8.0, EDTA 1 mM). After the tail length had been checked as described (Carninci and Hayashizaki, 1999), the cDNA was employed in second-strand synthesis for use in verifying libraries (see below) or employed as cDNA tester for use innormalization and/or subtraction.

Normalization Drivers mRNA drivers comprising aliquots of starting mRNA are called "normalizing or normalization drivers." To calculate the concentration of the normalizing driver, the ribosomal/structural RNA contamination in the starting mRNA was approximated by assuming that the incorporation rate of the first-strand synthesis reflected the actual mRNA concentration, thus assuming 100 percent efficiency of priming and elongation. Assuming that the proportion of mRNA converted to first-strand cDNA corresponded to the actual mRNA concentration, less-than-full-length cDNAs were excluded from consideration. Although not all of the mRNA is normally primed, a slight excess of normalization driver seldom has as dramatic an effect as a paucity of driver. Therefore, it was assumed that the amount of mRNA in the sample was the same as the quantity of first-strand cDNA produced.

Subtraction Drivers

The subtractive drivers consisted of bulk run-off transcripts prepared from cloned minilibraries and rearrayed libraries prepared from the nonredundant RIKEN cDNA encyclopedia using T7 and T3 RNA polymerases.

The minilibraries contained approximately 1,000 to 2,000 clones of cDNA in the sample that were derived from previous normalization experiments conducted by the same methods as the experiment described in the present embodiment. Employing the standard protocol, minilibraries were prepared from the captured aliquot (abundant cDNA fraction) that was the by-product of normalization experiments. Following normalization, the abundant cDNA fraction was removed from the beads with 50 mM NaOH/5 mM EDTA. Following neutralization, second-strand cDNA was prepared. Cloning was accomplished in a manner analogous to what has been previously described (Carninci and Hayashizaki, 1999). Plasmid was then bulk-excised, and 1,000–2,000 clones per minilibrary were amplified on agarose/ampicillin. To prepare drivers, 20,000 to 50,000 colonies were plated (plate size 150 mm diameter) on SOB-agarose/ampicillin (Sambrook et al. 1989, "Molecular Cloning: A laboratory Manual" Cold Spring Harbor Laboratory Press, Cold Spring Harbor, N.Y.) and the plates were incubated overnight at 37° C. Bacterial cells were scraped from the plates in the presence of resuspension solution (Wizard DNA extraction kit; Promega) after which the manufacturer's protocol was followed.

Preparation of Nonredundant cDNA Library Driver

Single clones from full-length cDNAs obtained in previous experiments conducted in the same manner as described in the present embodiment were rearrayed for subtraction. Rearrayed cDNAs were coated from 384-well plates onto SOD agarose/ampicillin plates. Plasmid extraction, DNA cleavage, and RNA preparation were conducted in the same manner as for the minilibraries.

When the library had been cloned at the SstI site, the extracted plasmid was treated at multiple cloning sites on the 3'-end with SstI. (In the case of mRNA extracted from the liver and lungs, the minilibrary was cloned with XhoI at the 3'-end site, and PvuI was used.) RNA was synthesized using either T3 or T7 RNA polymerase (Life Technologies), depending on the map of the construct used to prepare the driver, to prepare sense run-off RNAs. T3 polymerase was employed for PvuI-cleaved minilibraries and T7 polymerase for SstI-cleaved minilibraries. RNA was prepared using RNA polymerases (Life Technologies) in accordance with the manufacturer's instructions. Extensive digestion with 1 to 2 μL of DNaseI (RQ1, RNase-free, Promega) was performed for 30 min. Proteinase K digestion was then conducted, followed by extraction with phenol/chloroform and chloroform, and cDNA was precipitated.

Biotin Labeling of Normalizing/Subtracting RNA Drivers

To further clean up RNA drivers before labelling, the RNeasy kit (QIAGEN) was employed in accordance with the manufacturer's instructions. Subsequently, the Mirus nucleic acid biotinylation kit (Panvera) was employed in essentially the manner described by the manufacturer. A 10 μg quantity of the RNA mix was labeled by combination with 10 μL of Label IT reagent and 10 μL of labeling buffer A to a final volume of 100 μL following the kit protocol instructions. The reaction was incubated at 37° C. for 1 hour, after which the biotinylated RNA was precipitated by adding 1/20-volume of 5M NaCl and two volumes of 99 percent ethanol. After standard ethanol precipitation, the pellet was washed once with 80 percent ethanol, resuspended in 20 μL of "1× Mirus labelling buffer A", and stored at −80° C. until use (alternatively, mRNA can be labelled using the psoralen-biotinylation kit (Ambion) in accordance with the manufacturer's instructions).

Normalization/Subtraction

The RNA drivers and cDNA were deproteinated using proteinase K followed by phenol/chloroform extraction, chloroform extraction, and ethanol precipitation. Oligo-dG-tailed cDNA was used as a substrate, which was mixed with the RNA drivers and blocking oligonucleotides (biotin-dG$_5$ to -dG$_{30}$, here biotin-dG$_{16}$ was used) to hybridize to the C-stretch present in the subtracting driver and with oligo-dT primer to block the polyA sequences. However, any oligonucleotide able to block common sequences between drivers and cDNAs can be used.

Hybridization was typically carried out at RoT values of 1 to 500 (RoT is defined in 1997 examples by Sagerstrom et al.) in a buffer containing 80 percent formamide (from a deionized stock), 250 mM NaCl, 25 mM HEPES (pH 7.5), and 5 mM EDTA. Hybridization was carried out at 42° C. in a dry oven; even volumes as small as 5 μL did not require mineral-oil overlays. After hybridization, the sample was precipitated by adding 2.5 volumes of absolute ethanol and incubated for 30 minutes on ice. The sample was then centrifuged for 10 min at 15,000 rpm and washed once with 70 percent ethanol; the cDNA (both single-strand cDNA and mRNA/single-strand cDNA hybrids) was carefully resuspended in 10 μL of water on ice.

Treatment with RNase I

As necessary, the tester/driver hybrids obtained in the above step can be treated with RNase I to remove the mRNA normalization and subtraction drivers bound nonspecifically to the tester cDNA.

After removing the supernatant from the sample, precipitated after hybridization as described above, the pellet was resuspended with 45 μL of double-distilled water or TE 0.1× (1 mM Tris, 0.1 mM EDTA, pH 7.5) on ice (to minimize nonspecific repeat annealing). The pellet was completely redissolved before proceeding to the next step.

A 5 μL quantity of 10× RNase I Buffer (Promega) and 0.5 unit of RNase I were then added per 10 μg of driver RNA. The mixture was incubated at 37° C. for 10 min, heated at 65° C. for 10 min, and placed on ice. (As necessary, the samples can be treated with proteinase K, phenol/chloroform, and chloroform, and precipitated with ethanol before proceeding to the next step).

Removal of Hybrid

The next step can be applied to the normalized/subtracted mixture whether or not it has been treated with RNase I as indicated in the above step.

Separately, 50 μL of MPG-strepavidin magnetic beads (CPG Inc.) were prepared for each 1 μg of biotinylated driver RNA; a 5 μL quantity of beads was found to be capable of binding more than 400 ng of biotinylated driver. To each 50 μl of beads was added 10 μg of tRNA as a blocking reagent and the beads were incubated at room temperature for 10 to 20 min or on ice for 30 to 60 min with occasional shaking. A magnetic stand was employed to remove the beads, which were washed three times with a large excess of 1 M NaCl and 10 mM EDTA and resuspended in a volume of 1M NaCl and 10 mM EDTA equivalent to the original volume of the bead suspension.

The blocked beads were mixed with the redissolved tester/driver mixture and the entire sample was incubated at room temperature for 15 min with occasional gentle mixing. After removing the beads using a magnetic stand for 3 min, the supernatant, which contained the single-strand normalized/subtracted cDNA, was recovered. The beads were washed once with an excess volume of binding buffer (1M NaCl, 10 mM EDTA) to recover any remaining ssDNA. The radioactivity of the labeled samples was measured before and after the procedure in order to estimate the yield of normalization/subtraction.

Microcon 100 ultrafiltration was employed as described by the manufacturer (Millipore) to concentrate the cDNA solution to approximately 50 μL. Subsequently, the cDNA was pelleted by the standard isopropanol procedure. The pellet was resuspended in 44 μl of 0.1×TE, to which 5 μL of RNase I buffer and 1 U of RNase I were added to make a volume of 50 μL. The samples were then incubated for 20 min at 37° C., after which 400 μL of 0.2 percent SDS was added to inactivate the RNase I. Traces of degraded RNAs, blocking oligonucleotide, SDS, and buffer were removed by ultrafiltration with a Microcon 100 filter at 2,000 rpm and 25° C. until the volumes were reduced to less than 20 μL. The samples were desalted by adding 400 μl of 0.1×TE then centrifuging as above for a total of three washes. The cDNA was recovered by inverting the filter in a new tube and centrifuging at 9,000 rpm for 1 min.

Synthesis of Second-Strand cDNA

The second-strand synthesis and cloning steps were identical for normalized/subtracted cDNA, the standard control libraries, and the minilibraries. In the same manner as for the first-strand cDNA primer, a XhoI-containing primer, 5'-

(GA)$_7$TTCTCGAGTTAATTAAATTAATC$_{13}$-3' (SEQ ID NO:2), was prepared and purified by standard techniques.

To prepare the second-strand reaction, oligo-dG-tailed cDNA was mixed with 6 μL of 100 ng/μL second-strand primer adapter, 6 μL of EX-Taq second-strand buffer (Takara), and 6 μL of 2.5 mM (each) dNTPs. The reagents were combined with enzyme at 50° C. (usually from 45° C. to about 80° C.) to ensure high specificity of priming (called "hot start"). Priming was then conducted by adding 3 μL of 5 U/μL ExTaq polymerase (Takara) at 65° C. in a thermocycler. After mixing, the annealing temperature was set by a negative ramp to 45° C. for the XhoI primer (35° C. for the SstI primer in case of liver and lung libraries of Example 2). After 10 minutes at the annealing temperature, the second-strand cDNA was extended during incubation at 68° C. for 20 min. The annealing-extension cycle was repeated once more, followed by a final elongation step at 72° C. for 10 min. At the beginning of the hot start, a 5 μL aliquot was mixed with 0.5 μL of [alpha$^{32}$P]dGTP or [alpha$^{32}$P]dCTP and incorporated. The labeled aliquot was employed at the end of the reaction to measure the cDNA and to calculate the second-strand yield (Carninci and Hayashizaki, 1999).

Cloning of cDNA

Second-strand cDNA was treated with proteinase K, extracted with phenol-chloroform and chloroform, and ethanol-precipitated in accordance with standard procedures. The cDNA was then cleaved using 25 U/μg each of BamHI and XhoI (or SstI and XhoI for lung and liver libraries of Example 2). Following digestion, cDNA was treated with proteinase K, extracted with phenol-chloroform, and purified on a CL-4B spin column (Pharmacia). After ethanol precipitation, the cDNA was cloned essentially as described in the literature (Carninci and Hayashizaki, 1999).

Methodology and Equipment Utilized

Plaque hybridization was conducted with random primer and labeled specific probes in accordance with standard protocols (Sambrook et al. 1989).

Alkali electrophoresis was performed as described in the literature (Sambrook et al. 1989). All autoradiography signals were visually displayed using the Bas 2000 imaging system (Fuji).

Bacteria were collected with commercially available picking machines (Q-bot and Q-pix; Genetics, UK) and transferred to 384-microwell plates.

Duplicate plates were used to prepare plasmid DNA. The plasmid DNA from each of the 384-well plates was divided and grown in four 96-deepwell plates. After overnight growth, plasmids were extracted either manually (Itoh et al. 1997, Nucleic Acids Res 25:1315–1316) or automatically (Itoh et al. 1999, Genome Res. 9:463–470).

Sequences were typically run on a RISA sequencing unit (Shimadzu, JAPAN) or using the Perkin Elmer-Applied Biosystems ABI 377 in accordance with standard sequencing methodologies such as described by Hillier et al., 1996, Genome Research, 6:807–828. The sequencing primers were the M13 forward and reverse primers (above described SEQ ID NO: 5 and SEQ ID NO: 6).

EXAMPLE 2

Lung and Liver Tissues cDNA normalized/subtracted libraries (and minilibraries) were prepared from lung and liver tissues in the same manner as described in Embodiment 1 for brain tissue, with the exception that a primer containing an XhoI site (5'(GA)$_8$ACTCGAG(T)$_{16}$VN-3') (SEQ ID NO: 4) and an SstI-containing primer 5'-(GA)$_9$GAGCTCACTAGTTTAAT-TAAATTAATC$_{11}$-3' (SEQ ID NO: 3) were employed for mRNA extracted from liver and lung tissues. The other steps were the same as those described for brain tissue.

EXAMPLE 3

Efficiency of Removal in Driver/Tester Capture

Preparation of an RNA Template

A pBluescript plasmid containing a 5 Kb fragment of reeler cDNA (Hirotsune et al., Nature Genetics, 1995, May, 10(:77–83)) was employed.

From 2.5 μL of template plasmid DNA (cleaved at the NotI restriction site), RNA was transcribed in vitro under standard conditions: 20 μL of Gibco-BRL 5× buffer, 5 μL of rNTPs (10 mM each), 5 μL of 0.1M DTT, and 20 Units of T7 RNA polymerase at a final volume of 100 μL. The reaction was conducted by incubation at 37° C. for 3 hours. Also, 2 μL of alpha-$^{32}$P-rUTP was added in the reaction to label the RNA.

Subsequently, 20 units of RQ1 DNase (Promega) were added to remove trace quantities of template DNA (plasmid) and the sample obtained was incubated at 37° C. for 15 min. NaCl was added to the sample to a final concentration of 250 mM. The sample obtained was deproteinated once with phenol (equilibrated with Tris)/chloroform and once with chloroform. Two volumes of ethanol RNA were then added to precipitate RNA. After centrifugation for 20 min at 15,000 rpm, the precipitated RNA was separated from the supernatant. The precipitate was washed once with 70 percent ethanol, followed by centrifugation. The pellet was then redissolved in water.

Preparation of cDNA (Tester)

cDNA was prepared from the RNA template as specified in the instruction manual of Superscript II (Gibco BRL-Life Technology), with the exception that the primer that was specific to the clone was SK primer (5'CGCTCTAGAAC-TAGTGGATC3')(SEQ ID NO:7) and that alpha-$^{32}$ P dGTP was used to label the first strand for later tracing. Following phenol/chloroform extraction and ethanol precipitation in accordance with standard procedures, the cDNA was treated with alkali (50 mM NaOH for 30 min) to remove the hydrolized, hybridized RNA and neutralized with 200 mM Tris at pH 7.00. A 20 U quantity of RNase I was added. In the end, the DNA was again extracted with phenol/chloroform and precipitated with ethanol under standard conditions.

Biotinylation of RNA

The RNA template was also employed as a driver. Aliquots of 500 ng of RNA were biotinylated with a biotin-psoralen kit (Ambion) on ice (samples 1–3) or at room temperature (samples 4–6) for 30 min (1, 4), 45 min (2, 5) and 60 min (3, 6) (see FIG. 6).

Following biotinylation, 50 ng of cDNA (6,000 CPM) and 10 μg of tRNA were added to 150 ng of biotinylated driver (prepared under conditions 1–6, thus employing 6 tubes) (counting 21,000 CPM). After standard phenol/chloroform extraction and ethanol precipitation, the samples were redissolved in 5 μL of hybridization buffer (80 percent formamide, 250 mM NaCl, 25 Mm Hepes pH 7.5, 5 mM EDTA) and incubated at 42° C. overnight (14 hours).

Following ethanol precipitation (conducted in the same manner in the other embodiments), the samples (6 tubes) were then mixed with streptavidin/magnetic [beads] (the subtraction step described in Embodiment 1). The supernatant (unbound) was then precipitated with ethanol under standard conditions with the addition of 4 μg of glycogen to ensure quantitative precipitation, and after resuspension, loaded on a standard RNA/formaldehyde minigel (lanes 1–6). After 1 hour of electrophoresis at 60 V, the gel was dried and exposed with the Bas 2000 image analyzer (Fuji). This showed the efficiency of removal of driver and tester. The (lanes 7–9) side was employed for untreated sample (mRNA/cDNA) corresponding to 10 percent and 2 percent of the starting count of 100. The intensity of the signal indicated the efficiency of removal of the driver/tester mixture.

EXAMPLE 4

Methods of Evaluating the Invention

Reduction in the Frequency of Abundant cDNAs

Several normalized/subtracted cDNA libraries were prepared from pancreas tissue in the same manner as described above for brain tissue using RNA drivers and minilibraries derived from the rearrayed nonredundant cDNAs prepared in the above-described embodiments to reduce unnecessary resequencing of clones already present.

Figure 3:
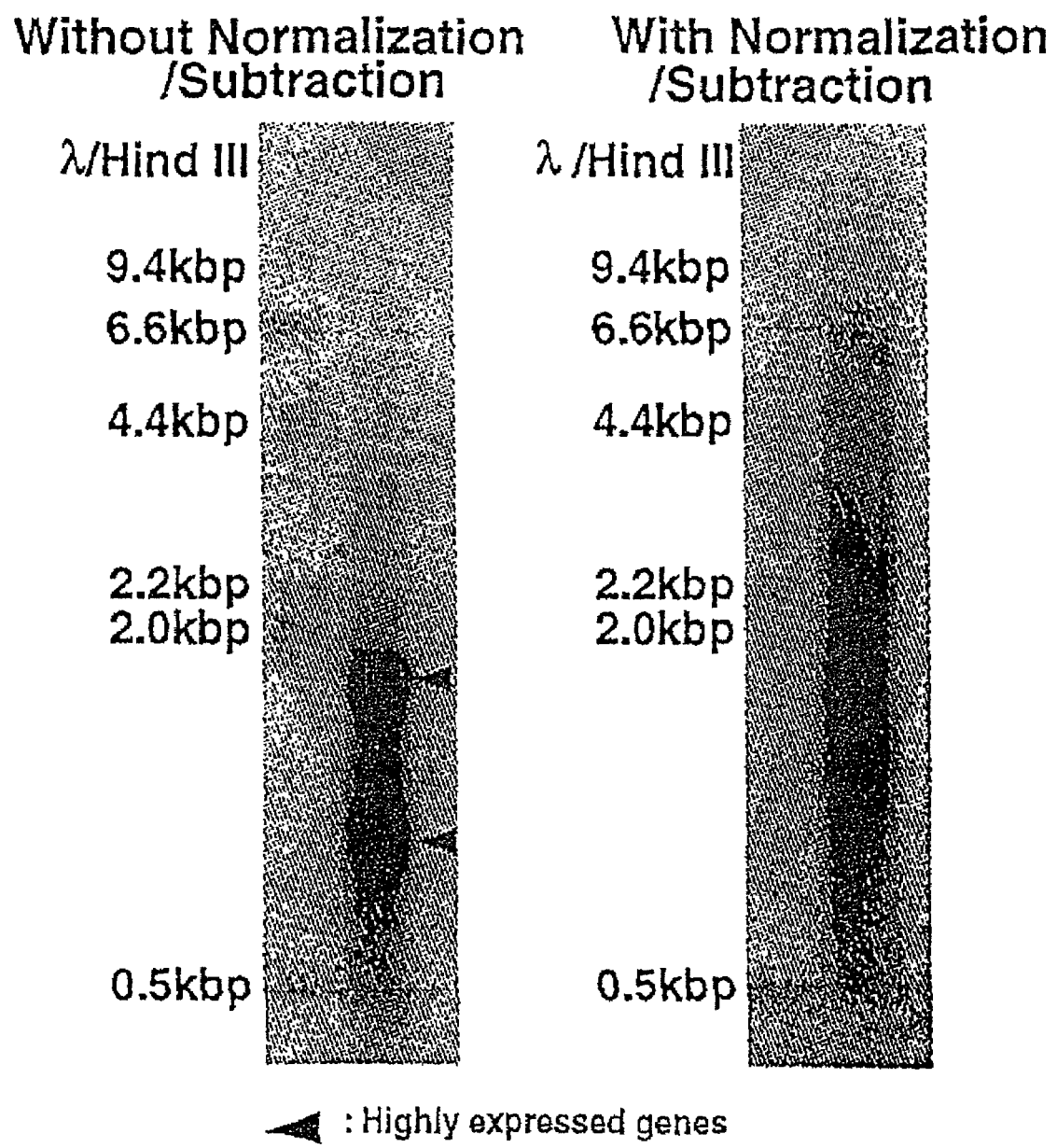
FIG. 3 shows on the right side an electrophoretic pattern of pancreas cDNA normalization/subtraction performed in one single step compared with a run of pancrease cDNA that has not been normalized/subtracted. This example of normalization/subtraction provides a visual image of the removal of highly abundant full-length cDNAs, which are visible in the example of cDNA that has not been normalized/subtracted (indicated by arrow).

The second-strand cDNA from a standard pancreas cDNA library (without normalization/subtraction) was compared to its normalized/subtracted counterpart (FIG. 3). The normalized/subtracted cDNA was prepared in a single normalization/subtraction step. Normalization was performed at RoT=10, and subtraction was conducted using a set of minilibraries prepared as set forth above at RoT=20 (subtraction can be performed at an RoT value of up to around 500) each of which contained 1,000 to 2,000 redundant mostly abundant clones from liver, lung, brain, or placenta tissue. The minilibraries were generated by cloning the highly expressed fractions of previously prepared, normalized cDNA libraries. Amplified cDNA minilibraries were then used to prepare the subtracting drivers (as described above). The RoT of the subtracting drivers equaled 1 unit for every 200 clones (e.g., RoT=5 when 1,000 clones were employed). The average length of normalized, subtracted cDNA was greater than that of non-normalized, non-subtracted cDNA, suggesting that long cDNAs (which migrate more slowly) are expressed more rarely than the shortest cDNAs. In addition, bands corresponding to cDNAs of highly expressed mRNAs were not visible from the normalized-subtracted library.

FIG. 3 shows an electrophoresis run without normalization/subtraction (standard cDNA). A few highly intense bands derived from superabundant RNAs are visible. By contrast, in the normalized-subtracted cDNA, those bands are no longer visible, suggesting a decrease in the cDNA. Moreover, in the normalized/subtracted cDNA, the relative intensity of cDNAs corresponding to long mRNAs (>~3 Kb) is greater than in the standard libraries.

Figure 4:
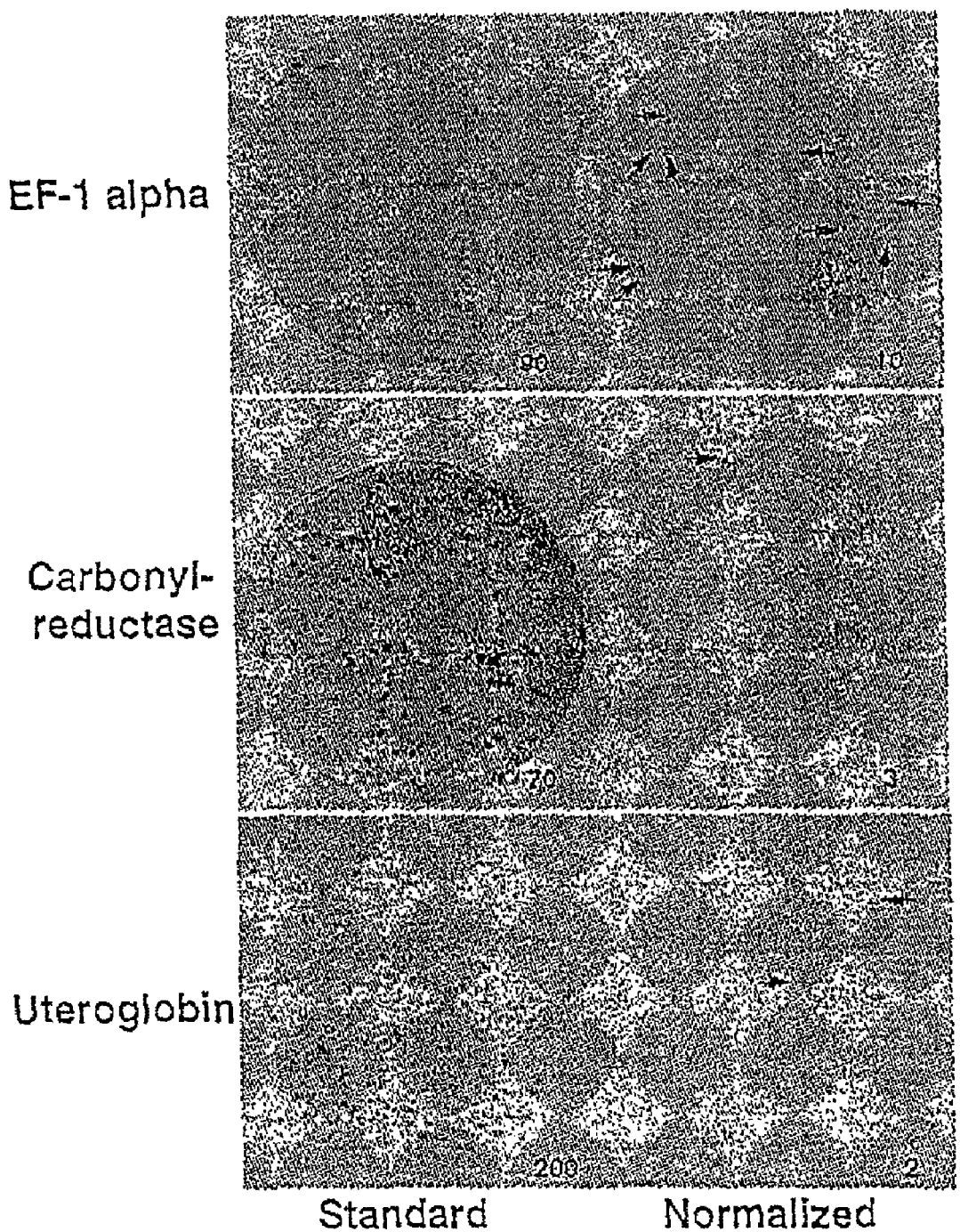
FIG. 4 shows results of plaque hybridization of replicas for the genes EF-1 alpha, carbonyl-reductase and uteroglobin containing a standard (not normalized and not subtracted) length cDNA library (left) or a normalized length cDNA library (right). On the right panel (normalized), the arrow indicates the plaques that have been counted. The number of plaques (clones) counted for the normalized library is sensitively lower than that for the standard library.

Another way of demonstrating the advantages of normalization/subtraction is shown in FIG. 4.

First-strand lung cDNA prepared as described above was employed as template. Genes that were abundantly expressed in plaque hybridization functionally corresponding to a normalized cDNA library decreased in the normalized library. When 10,000 plaques of the normalized lung library were screened, elongation factor 1-alpha went from 90 plaques in the reference library to 10 in the normalized library. Carbonyl reductase decreased from about 70 plaques to 3. And uteroglobin was reduced from about 510 plaques to 2. The plaques were counted. There were more plaques in the standard cDNA libraries (about 10 times more in the standard library than in the normalized library). These results demonstrated that the frequency of abundantly expressed cDNAs in the normalized library was much lower than in the control.

EXAMPLE 5

Increasing the Frequency of Discovery of Rare Genes

Large-scale library sequencing is the best way to test the concentration of rare cDNAs. A number of libraries (Table 1) were prepared from several mouse tissues by the method set forth above and assessed by checking the average size of the cDNA inserts (insert size), sequences passes (Seq.), clusters (Sp.), redundancy (Red.), appearance of new clones (Unique), and presence of full-coding/length cDNA based on the percent of sequences having the first ATG codon (coding percent).

TABLE 1

| Library ID | Development Stage/ tissue | Normalizing Driver (Rot) | Insertion Size (kbp) | Seq. | Sp. | Red. | Unique (%) | Coding (%) |
|---|---|---|---|---|---|---|---|---|
| 18-100 | Adult/pancreas | mRNA(5) | 1.2 | 13556 | 3402 | 3.98 | 442 (13.0) | (100.0) |
| 22-000 | adult/stomach | (standard) | 0.88 | 1458 | 488 | 2.99 | 42 (8.6) | (82.1) |
| 22-100 | | mRNA(5) | 1.21 | 4400 | 1932 | 2.28 | 196 (10.1) | (82.1) |
| 22-104 | | mRNA(5) | 1.13 | 3639 | 1852 | 2.11 | 207 (11.1) | (82.1) |
| 23-000 | Adult/tongue | (standard) | | 1179 | 556 | 2.12 | 36 (6.5) | 76.8 |
| 23-100 | | mRNA(5) | 1.44 | 10267 | 4017 | 2.56 | 586 (14.6) | 76.8 |
| 24-100 | ES cell | mRNA(5) | 1.77 | 15226 | 4495 | 3.89 | 485 (10.8) | (88.6) |
| 25-100 | Embryo13/liver | mRNA(5) | 1.19 | 5448 | 1525 | 3.57 | 168 (11.0) | 92.2 |
| 26-000 | Embryo10/ | (standard) | 1.38 | 2108 | 1061 | 1.99 | 71 (6.7) | 92.3 |
| 26-100 | whole body | mRNA(7.5) | 1.32 | 11267 | 4722 | 2.99 | 582 (12.3) | 92.3 |
| 28-100 | Embryo10 + 11/ | mRNA(7.5) | 1.29 | 6248 | 3411 | 1.83 | 271 (7.9) | (93.9) |
| 28-104 | whole body | mRNA(7.5) | 1.38 | 9321 | 4335 | 2.15 | 453 (10.4) | (93.9) |
| 31-000 | Embryo/ | (standard) | 1.22 | 488 | 369 | 1.32 | 23 (6.2) | (86.2) |
| 31-100 | head | mRNA(10) | 1.55 | 7838 | 4229 | 1.85 | 494 (11.7) | (86.2) |
| 32-304 | Embryo14 + 17/ head | mRNA(10) | 2.5 | 424 | 389 | 1.09 | 20 (5.1) | (88.2) |

TABLE 1-continued

| Library ID | Development Stage/ tissue | Normalizing Driver (Rot) | Insertion Size (kbp) | Seq. | Sp. | Red. | Unique (%) | Coding (%) |
|---|---|---|---|---|---|---|---|---|
| 38-304 | Embryo 11/ placenta & extraembryon tissue | mRNA(10) | 1.45 | 3657 | 2165 | 1.69 | 156 (7.2) | (100.0) |
| 39-304 | Embryo13/ whole body | mRNA(10) | 2.47 | 348 | 319 | 1.09 | 22 (6.9) | (90.0) |
| 49-304 | Adult/testis | mRNA(10) | 2.11 | 8900 | 5444 | 1.63 | 1214 (22.3) | (95.7) |
| 52-304 | Adult/ Xiphold | total RNA(3) | 2.69 | 272 | 256 | 1.09 | 15 (5.9) | (100.0) |
| 53-304 | Adult/pituitary gland | total RNA(3) | 2.38 | 8059 | 4858 | 1.73 | 833 (17.9) | (100.0) |
| 54-304 | Neonate6/ head | mRNA(10) | 2.3 | 2663 | 2101 | 1.27 | 196 (9.3) | (90.0) |
| 57-304 | Embryo8/ whole body | (subtracted only) | 1.91 | 19532 | 7758 | 2.53 | 1155 (14.9) | (100.0) |
| 58-304 | Adult/thymus | mRNA(10) | 3.27 | 10259 | 6442 | 1.59 | 1100 (17.1) | (80.0) |
| 60-304 | Embryo13/ testis | total RNA(5) | | 11079 | 6498 | 1.7 | 1243 (19.1) | (75.0) |
| 61-304 | Embryo14/ thymus | (subtracted only) | 4.13 | 206 | 196 | 1.05 | 16 (8.2) | (60.0) |
| 62-304 | Embryo11/head | mRNA(10) | 2.19 | 2957 | 2374 | 1.25 | 256 (10.8) | (70.0) |

Assessing the degree of sequence redundancy was the final evaluation of the efficiency of the normalization/subtraction process. Standard libraries (indicated by the reference numbers 22-000, 23-000, 26-000, and 31-000) prepared from an aliquot of the starting cDNA are shown for comparison (Table 1).

In one successfully normalized-subtracted cDNA library (library 49-304 from mouse testicular tissue), the redundancy of 3'-end sequences was as low as 1.63 (calculated by dividing the total number of clones sequenced, 8,900, by the number of different clusters, 5,444). It was anticipiated that redundancies of less than 2.0 in more than 10,000 to 15,000 3'-end sequences could be expected in successful cDNA libraries from complex tissues (e.g., testes, brain, and thymus).

Normalized/subtracted cDNA libraries facilitated efficient and increased recovery of unknown genes. For example, libraries 22-100, 23-100, 26-100, and 31-100 produced values of new data per sequencing reaction higher than standard library counterparts 22-000, 23-000, 26-000, and 31-000 (FIG. 5).

Figure 5:
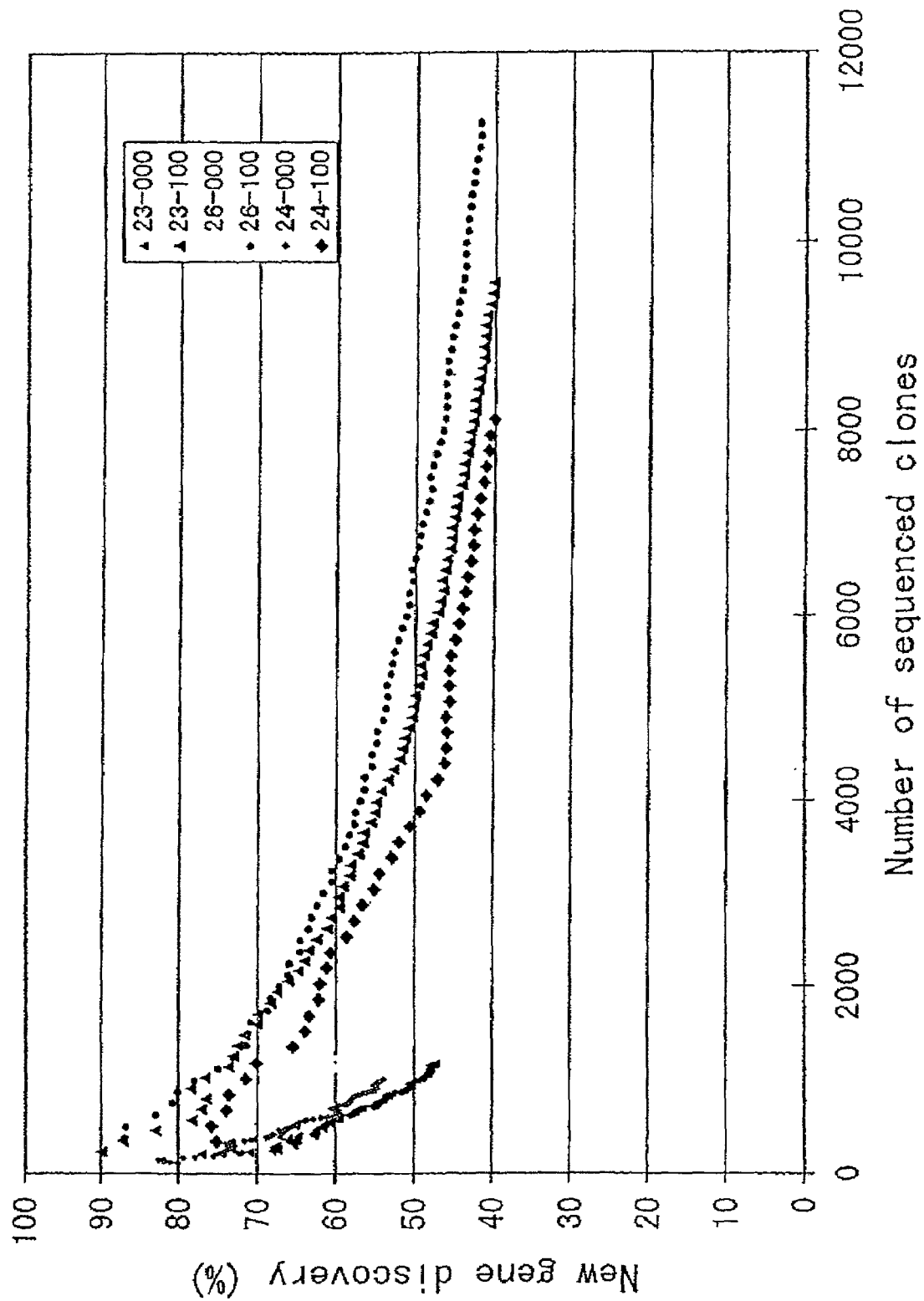
FIG. 5 shows results in which the increase in sequencing redundancy (or decrease in new gene discovery) increases sharply in standard cDNA libraries (-000 libraries), but in normalized/subtracted full-length cDNA libraries (-100 libraries) the increase in redundancy is quite slow. New genes (percent) are indicated as singletons (percent) within a given cDNA library.

Sequencing several cDNAs from several libraries revealed a decrease in sequence redundancy in the normalized-subtracted libraries as compared to the standard cDNA libraries (FIG. 5).

In FIG. 5, 100 percent new gene discovery corresponds to a redundancy value of 1, 50 percent corresponds to a redundancy value of 2, 25 percent corresponds to a redundancy value of 4, and so forth.

Normalization increases the frequency of new gene discovery relative to standard libraries during a given sequencing effort.

EXAMPLE 6

Comparative Example of the Normalization-Subtraction Methods of the Present Invention The importance of the use of an enzyme cleaving single-strand RNA (driver) bound nonspecifically to cDNA (tester) was checked. Accordingly, sub-libraries prepared by the normalization/subtraction method of the present invention were compared with sub-libraries prepared by the normalization/subtraction method and the step of removing non-specific hybrid.

Normalized/subtracted cDNAs prepared in accordance with the first part of Example 1 (through the portion including the normalization/subtraction step) were divided into two subtraction libraries. The first sublibrary was subjected to second strand cDNA synthesis and cloning (without removal of non-specifically bound hybrids), while the second library was subjected to the RNase I treatment (removal of non-specifically bound hybrids) described in Example 1. The mouse tissues prepared were as follows: medulla oblongata for library 63, olfactory brain for library 64, colon for library 90, and cecum for library 91. The data are reported in Table 2.

TABLE 2

| | Reference Number | | Cluster | Unique Clone | p/o Unique Clone | |
|---|---|---|---|---|---|---|
| −RNase I | 63-304-R | RISA | 2987 | 252 | (8.4) | 15.4% |
| +RNase I | 63-305-R | RISA | 5358 | 518 | (9.7) | |
| −RNase I | 64-304-R | RISA | 1258 | 80 | (6.4) | 81.1% |
| +RNase I | 64-305-R | RISA | 6371 | 742 | (11.6) | |
| −RNase I | 90-300-R | RISA | 1348 | 106 | (7.9) | 27.0% |
| +RNase I | 90-302-R | RISA | 779 | 72 | (9.2) | |
| −RNase I | 90-304-R | RISA | 1066 | 57 | (5.3) | 62.0% |
| +RNase I | 90-306-R | RISA | 1479 | 127 | (8.6) | |
| −RNase I | 91-300-R | RISA | 1470 | 95 | (6.5) | 11.5% |
| +RNase I | 91-302-R | RISA | 1786 | 134 | (7.5) | |

Sublibraries 63-304-R, 64-304-R, 90-300-R, 90-304-R, 91-300-R denote sublibraries that were not treated with RNase I.

Sublibraries 63-305-R, 64-305-R, 90-302-R, 90-306-R, 91-302-R denote sublibraries treated with RNase I.

The combinations of sublibraries belonging to the same library are: 63-304-R and 63-305-R; 64-304-R and 64-305-R; 90-300-R and 90-302-R; 90-304-R and 90-306-R; and 91-300-R and 91-302-R.

The number of clusters for each sublibrary denotes the number of different clones (that is, clusters) comprising the sublibrary. Each cluster can comprise one or more clones having the same sequence (that is, the same sequence picked up a number of times).

"Unique clones" indicate the number of new clones obtained from a sublibrary cluster that have not been previously sequenced.

The "percentage of unique clones" (for example, the value "8.4" for the sublibrary 63-304-R) denotes the number of unique clones discovered (for example, "252" for sublibrary 63-304-R) divided by the number of clusters ("2987" for sublibrary 63-304-R).

The data of Table 2 indicate that all tests of treatment with RNase I yielded high percentages of unique clones (for example, 15.4 percent for sublibraries 63-304-R and 63-305-R). This indicates that a number of undiscovered (unique) clones nonspecifically bound to mRNA driver were released from hybrids by the RNase I treatment, recovered, and discovered.

The clone sequences were run on a RISA sequencing unit (Shimadzu, JAPAN). M13 forward and reverse primers were employed as sequencing primers.

```
Forward: M13 oligo (5' TGTAAAACGACGGCCAGT 3')          (SEQ ID NO: 5);

reverse: 1233REV oligo (5' AGCGGATAACAATTTCACACAGGA 3')  (SEQ ID NO: 6).
```

Sequencing was conducted in accordance with a known standard sequencing protocol (Hillier et al., 1996, Genome Res., 6:807–828).

The invention claimed is:

1. A method of preparing normalized and/or subtracted cDNAs comprising the steps of:
   I) preparing uncloned full-length or full-coding length cDNA tester;
   II) preparing polynucleotide drivers for normalization and/or subtraction;
   III) conducting normalization and/or subtraction and removing tester/driver hybrids, non-specifically hybridized polynucleotide drivers and non-hybridized polynucleotide drivers; and
   IV) recovering the normalized and/or subtracted full-length or full-coding length cDNA.

2. The method of claim 1, wherein the cDNA tester of step I) is a reverse transcript of mRNA in the form of uncloned cDNA.

3. The method of claim 1 wherein said cDNA tester is single-stranded.

4. The method of claim 1, wherein in step III), normalization is conducted first, followed by subtraction.

5. The method of claim 1, wherein in step III), subtraction is conducted first, followed by normalization.

6. The method of claim 1, wherein in step III), said tester and normalization and subtraction drivers are mixed together and normalization and subtraction are conducted as a single step.

7. The method of claim 1, wherein step III) comprises the addition of an enzyme capable of cleaving single-stranded RNA driver nonspecifically bound to single-stranded cDNA and the cleaved single-stranded RNA driver is removed.

8. The method of claim 7 wherein said enzyme is single-strand-specific RNA endonuclease.

9. The method of claim 7 wherein said enzyme is either selected from the group consisting of RNase I, RNaseA, RNase4, RNaseT1, RNaseT2, RNase2, and RNase3, or comprises a mixture thereof.

10. The method of claim 7 wherein said enzyme is RNase I.

11. The method of claim 1, wherein said cDNA tester is prepared by CAP-trapping the 5' end of RNA.

12. The method of claim 1, wherein the preparation of said full-length or full-coding length cDNA tester comprises the following steps:
  (1) synthesizing first strand cDNA by means of reverse transcriptase forming mRNA/cDNA hybrids;
  (2) chemically binding a tag molecule to the diol structure of the 5' CAP($^{7Me}G_{ppp}N$) site of mRNA forming hybrids;
  (3) trapping full-length or full-coding length cDNA hybrids; and
  (4) removing single-stranded mRNA by digestion with an enzyme capable of cleaving single-stranded mRNA.

13. The method of claim 12 wherein said tag molecule is digoxigenin, biotin, avidin, or streptavidin.

14. The method of claim 1, wherein said polynucleotide driver for normalization and/or subtraction is RNA and/or DNA.

15. The method of claim 14, wherein said DNA driver is cDNA.

16. The method of claim 1, wherein said normalization driver comprises cellular mRNA from the same library, from the same tissue, or the same cDNA population as the cDNA to be normalized.

17. The method of claim 1, wherein said normalization driver comprises single-stranded cDNA obtained from the same library, the same tissue, or the same cDNA population as the cDNA to be normalized.

18. The method of claim 1, wherein said subtraction driver comprises cellular mRNA from a library, tissue, or cDNA population differing from the cDNA to be subtracted.

19. The method of claim 1, wherein said subtraction driver comprises single-stranded cDNA from a library, tissue, or cDNA population differing from the cDNA to be normalized.

20. The method of claim 1, further comprising a step V) of preparing a complementary strand of the recovered cDNA and cloning the resulting double-stranded cDNA.

21. A method of preparing normalized and/or subtracted full-length or full-coding length cDNAs comprising the steps of:
  I) preparing cDNA tester not cloned in a plasmid;
  II) preparing polynucleotide drivers for normalization and/or subtraction;
  III) conducting normalization and/or subtraction and removing tester/driver hybrids, non-specifically hybridized polynucleotide drivers and non-hybridized polynucleotide drivers; and
  IV) recovering the normalized and/or subtracted full-length or full-coding length cDNA.

22. The method of claim 21, wherein in step III), normalization is conducted first, followed by subtraction.

23. The method of claim 21, wherein in step III), subtraction is conducted first, followed by normalization.

24. The method of claim 21, wherein in step III), said tester and normalization and subtraction drivers are mixed together and normalization and subtraction are conducted as a single step.

25. The method of claim 21, wherein step III) comprises the addition of an enzyme that cleaves single-stranded RNA driver nonspecifically bound to single-stranded cDNA and the cleaved single-stranded RNA driver is removed.

26. The method of claim 25, wherein said enzyme is single-strand-specific RNA endonuclease.

27. The method of claim 25, wherein said enzyme is either selected from the group consisting of RNase I, RNaseA, RNase4, RNaseT1, RNaseT2, RNase2, and RNase3, or comprises a mixture thereof.

28. The method of claim 25, wherein said enzyme is RNase I.

29. The method of claim 21, wherein said cDNA tester is prepared by CAP-trapping the 5' end of RNA.

30. The method of claim 21, wherein said normalization driver comprises cellular mRNA from the same library, the same tissue, or the same cDNA population the cDNA is to be normalized.

31. The method of claim 21, wherein said normalization driver comprises single-stranded cDNA obtained from the same library, the same tissue, or the same cDNA population as the cDNA to be normalized.

32. The method of claim 21, wherein said subtraction driver comprises cellular mRNA from a library, tissue, or cDNA population differing from the cDNA to be subtracted.

33. The method of claim 21, wherein said subtraction driver comprises single-stranded cDNA from a library, tissue, or cDNA population differing from the cDNA to be normalized.

34. The method of claim 21, further comprising a step V) of preparing a complementary strand of the recovered full-length or full-coding length cDNA and cloning the resulting double-stranded full-length or full-coding length cDNA.

35. A method of preparing normalized and subtracted full-length or full-coding length cDNA comprising the steps of:
  I) preparing cDNA tester;
  II) preparing polynucleotide drivers for normalization and subtraction;
  III) conducting the normalization and subtraction as a single step by mixing together the tester and the drivers; IV) removing non-specifically hybridized polynucleotide drivers; and
  V) recovering the normalized and subtracted full-length or full-coding length cDNA.

36. The method of claim 35, wherein the cDNA tester is cloned or uncloned cDNA.

37. The method of claim 35, wherein the cDNA tester is the reverse transcript of mRNA in the form of uncloned cDNA.

38. The method of claim 35, wherein the cDNA tester is single-stranded.

39. The method of claim 35, wherein step IV) comprises the addition of an enzyme capable of cleaving single-strand RNA driver nonspecifically bound to single-stranded cDNA and the cleaved single-stranded RNA driver is removed.

40. The method of claim 39, wherein said enzyme is single-strand-specific RNA endonuclease.

41. The method of claim 39, wherein said enzyme is either selected from the group consisting of RNase I, RNaseA, RNase4, RNaseT1, RNaseT2, RNase2, and RNase3, or comprises a mixture thereof.

42. The method of claim 39, wherein said enzyme is RNase I.

43. The method of claim 35, wherein said cDNA tester is prepared by CAP-trapping 5' end of RNA.

44. The method of claim 35, wherein the preparation of said full-length or full-coding length cDNA tester comprises the following steps:
  (1) synthesizing first strand cDNA by means of reverse transcriptase forming mRNA/cDNA hybrids;
  (2) chemically binding a tag molecule to the diol structure of the 5' CAP($^{7Me}G_{ppp}N$) site of mRNA forming hybrids;
  (3) trapping full-length or full-coding length cDNA hybrids; and
  (4) removing single-stranded mRNA by digestion with an enzyme that cleaves single-stranded mRNA.

45. The method of claim 44, wherein said tag molecule is digoxigenin, biotin, avidin, or streptavidin.

46. The method of claim 35, wherein said polynucleotide driver for normalization and/or subtraction is RNA and/or DNA.

47. The method of claim 46, wherein said DNA driver is cDNA.

48. The method of claim 35, wherein said normalization driver comprises cellular mRNA from the same library, the same tissue, or the same cDNA population as the cDNA to be normalized.

49. The method of claim 35, wherein said normalization driver comprises single-stranded cDNA obtained from the same library, the same tissue, or the same cDNA population as the cDNA to be normalized.

50. The method of claim 35, wherein said subtraction driver comprises cellular mRNA from a library, tissue, or cDNA population differing from the cDNA to be subtracted.

51. The method of claim 35, wherein said subtraction driver comprises single-stranded cDNA from a library, tissue, or cDNA population differing from the cDNA to be normalized.

52. The method of claim 35, further comprising a step VI) of preparing a complementary strand of the recovered full-length or full-coding length cDNA and cloning the resulting double-stranded full-length or full-coding length cDNA.

53. A method of preparing normalized and/or subtracted full-length or full-coding length cDNA comprising the steps of:
  (a) preparing cDNA tester;
  (b) preparing normalization and/or subtraction RNA driver;
  (c) conducting normalization and/or subtraction in two steps in any order, or conducting normalization/subtraction as a single step and mixing the normalization/subtraction RNA driver with said cDNA tester;
  (d) adding an enzyme that cleaves single-stranded sites on RNA drivers non-specifically bound to cDNA tester;
  (e) removing said single-stranded RNA driver cleaved in step d) from the tester and removing tester/driver hybrids; and
  (f) recovering the normalized and/or subtracted full-length or full-coding length cDNA.

54. The method of claim 53, wherein the cDNA tester is cloned or uncloned cDNA.

55. The method of claim 53, wherein the cDNA tester is a reverse transcript of mRNA in the form of uncloned cDNA.

56. The method of claim 53, wherein said cDNA tester is single-stranded.

57. The method of claim 53, wherein in step c), normalization is conducted first, followed by subtraction.

58. The method of claim 53, wherein in step c), subtraction is conducted first, followed by normalization.

59. The method of claim 53, wherein in step c), said tester and normalization and subtraction drivers are mixed together and normalization and subtraction are conducted as a single step.

60. The method of claim 53, wherein said normalized and/or subtracted cDNA is full-length or full-coding length cDNA.

61. The method of claim 53, wherein the enzyme of said step d) is either selected from the group consisting of RNase I, RNaseA, RNase4, RNaseT1, RNaseT2, RNase2, and RNase3, or comprises a mixture thereof.

62. The method of claim 53, wherein the enzyme of said step d) is RNase I.

63. The method of claim 53, wherein said cDNA tester is prepared by CAP-trapping the 5' end of RNA.

64. The method of claim 53, further comprising the step g) of preparing a complementary strand of the recovered cDNA and cloning the resulting double-stranded cDNA.

65. The method of claim 1, wherein said tester/driver hybrids are bound to tag molecules.

66. The method of claim 65, wherein said tag molecule is avidin, streptavidin, biotin, digoxigenin, an antibody, or an antigen.

67. The method of claim 1, wherein said tester/driver hybrids are removed through the use of a matrix.

68. The method of claim 67, wherein said matrix is comprised of magnetic beads or agarose beads.

69. The method of claim 68, wherein said magnetic beads or agarose beads are covered by or bound to a tag molecule that binds to a tag molecule bound to a tester/driver hybrid.

70. The method of claim 68, wherein said magnetic beads or agarose beads are covered by or bound to a tag molecule that binds to avidin, streptavidin, biotin, digoxigenin, an antibody, or an antigen bound to a tester/driver hybrid.

71. The method of claim 69, wherein said tag molecule covering said beads or bound to said beads is an antiantigen antibody, antibiotin antibody, antiavidin antibody, antistreptavidin antibody, or antidigoxigenin antibody.

72. The method of claim 1, wherein said tester/driver hybrid is removed using streptavidin/phenol.

73. The method of claim 1, wherein hydroxyapatite and nonlabeled RNA are employed to remove said tester/driver hybrid.

74. The method of claim 1 employed to prepare one, two, or more libraries.

75. The method of claim 1, in which subtraction is performed and normalization is performed to a $R_0T$ value of from 5 to 10.

76. The method of claim 12, wherein the chemical tagging is performed on ice.

* * * * *